United States Patent [19]

Butler et al.

[11] Patent Number: 4,759,228

[45] Date of Patent: Jul. 26, 1988

[54] PROCESS FOR DETERMINATION OF REPELLENCY AND ATTRACTANCY

[75] Inventors: Jerry F. Butler, Gainesville, Fla.; Ira Katz, West Long Branch, N.J.

[73] Assignees: International Flavors & Fragrances Inc., New York, N.Y.; The University of Florida, Gainesville, Fla.

[21] Appl. No.: 114,424

[22] Filed: Oct. 29, 1987

Related U.S. Application Data

[60] Division of Ser. No. 002,023, Jan. 9, 1987, which is a continuation-in-part of Ser. No. 879,426, Jun. 27, 1986, Pat. No. 4,693,890.

[51] Int. Cl.⁴ ............................................. G01N 33/00
[52] U.S. Cl. ........................................ 73/866; 424/84; 514/919
[58] Field of Search .................... 73/432.1, 866, 865.2; 424/9, 84, DIG. 10, DIG. 11, 2; 514/919

[56] References Cited

U.S. PATENT DOCUMENTS

| | | | |
|---|---|---|---|
| 2,043,941 | 6/1936 | Williams | 514/706 |
| 2,254,665 | 9/1941 | Ralston et al. | 514/724 |
| 3,252,858 | 5/1966 | Goodhue | 514/919 X |
| 3,572,131 | 3/1971 | Wright et al. | 73/866 |
| 4,152,422 | 5/1979 | Ohinata et al. | 424/84 |
| 4,364,931 | 12/1982 | Szantay et al. | 424/84 |
| 4,449,987 | 5/1984 | Lindauer | 252/522 A |
| 4,693,890 | 9/1987 | Wilson et al. | 424/78 |
| 4,696,676 | 9/1987 | Wilson et al. | 424/78 X |

Primary Examiner—Tom Noland
Attorney, Agent, or Firm—Arthur L. Liberman

[57] ABSTRACT

Described is the use of 1-nonen-3-ol as a repellent for house flies (*Musca domestica*). Also described are candle compositions which may be opaque or transparent or pastel shaded which are adapted to incorporate 1-nonen-3-ol which are both perfumes and insect repellents without flashing during burning. Such compositions comprising as the basic components a mixture of (a) a hydrocarbon wax or (b) a thermoplastic polyamide resin formed from linoleic acid polymerized with a polyamide compound taken together with an alkanol amide or alkanol amine and as stearic acid compound or (c) a straight chain aliphatic amide in combination with light mineral oil and alcohol; compositions (a), (b) or (c), supra, taken further together with 1-nonen-3-ol taken alone or together with a perfume composition substantially inactive from an insect repellent standpoint. Also described is apparatus also referred to herein as an "olfactometer" used for measuring the repellency of said 1-nonen-3-ol. Also described herein is a process for the determination of the repellency of said 1-nonen-3-ol using said "olfactometer".

8 Claims, 22 Drawing Sheets

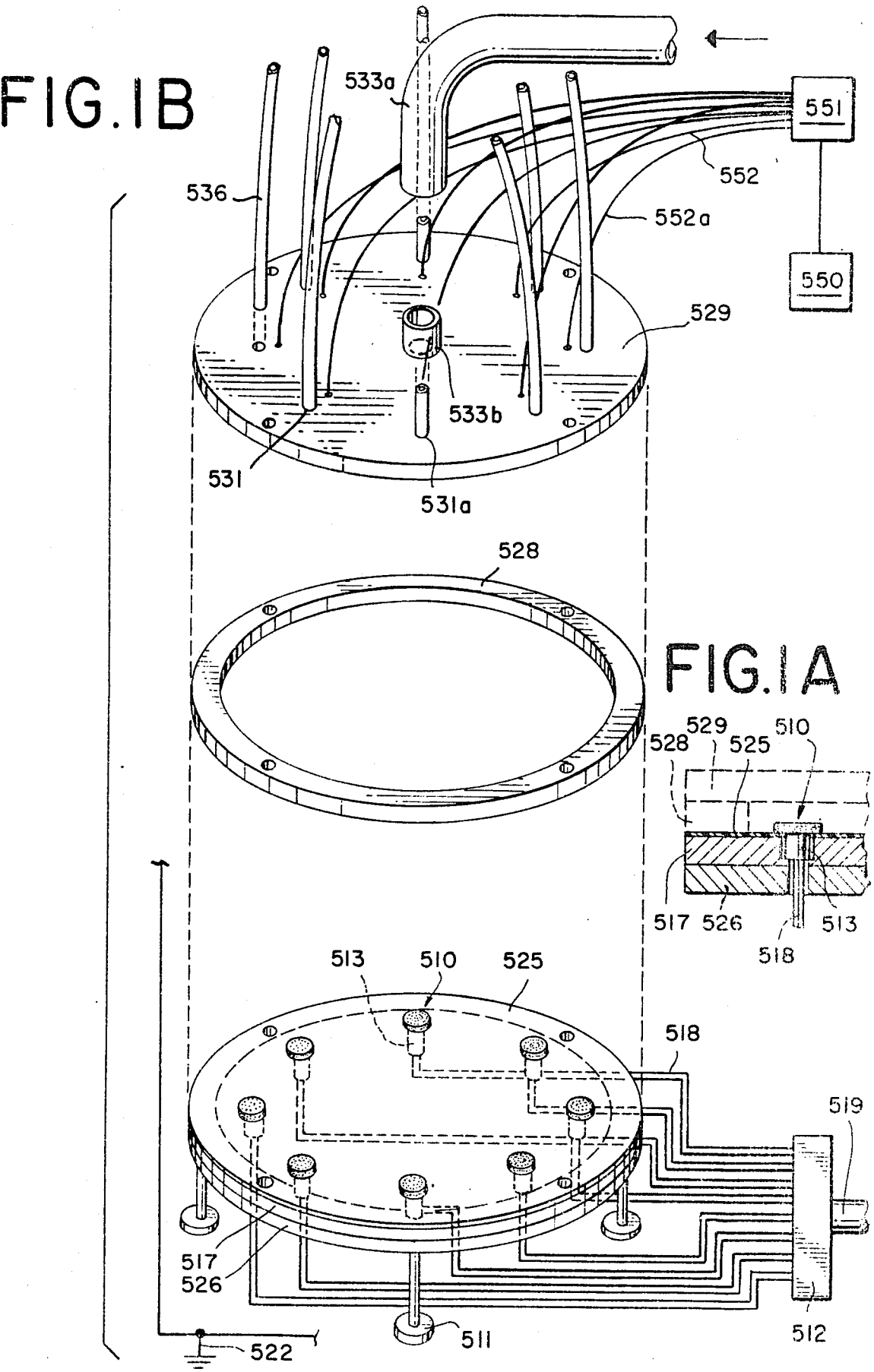

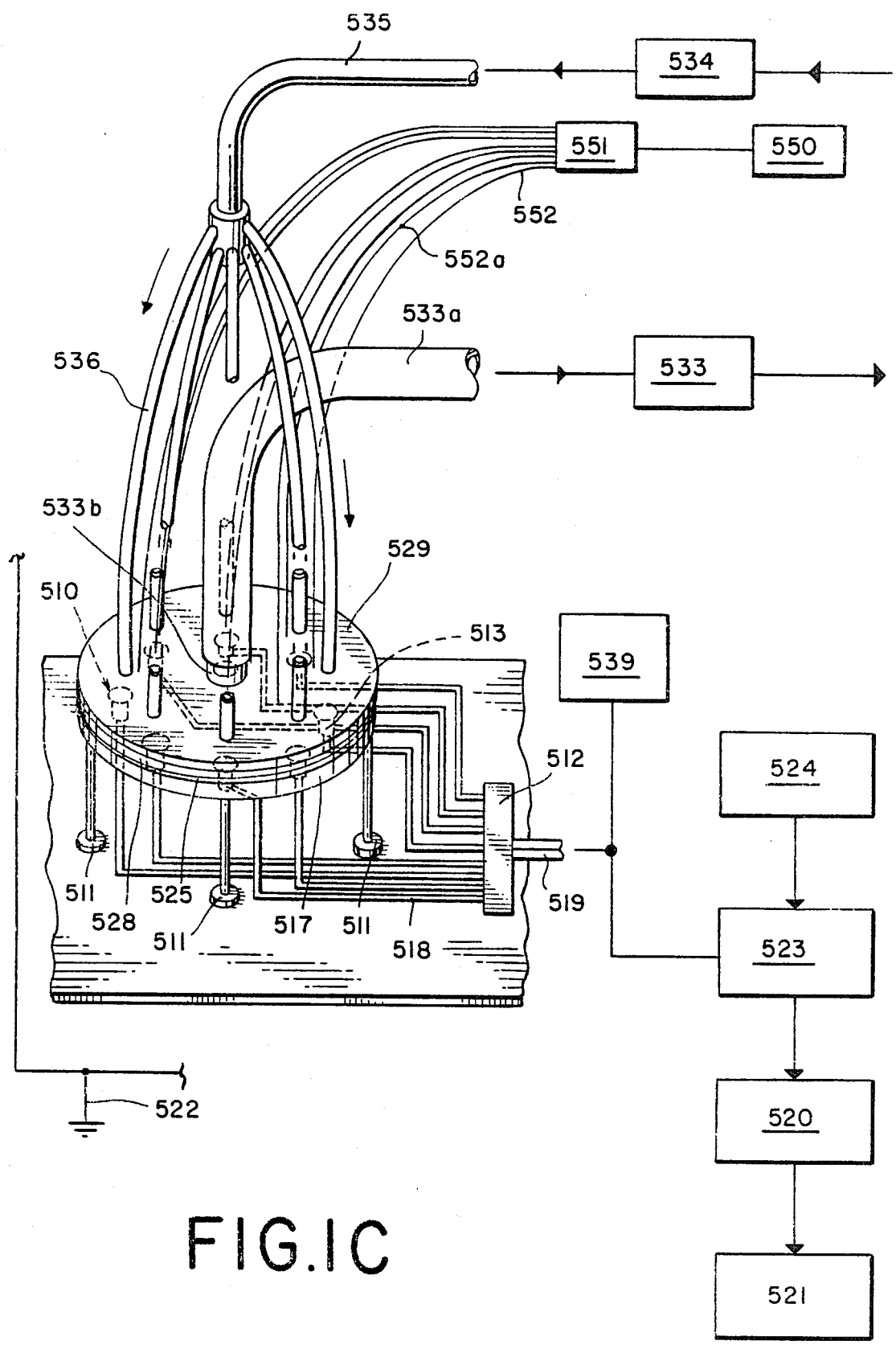
FIG.IC

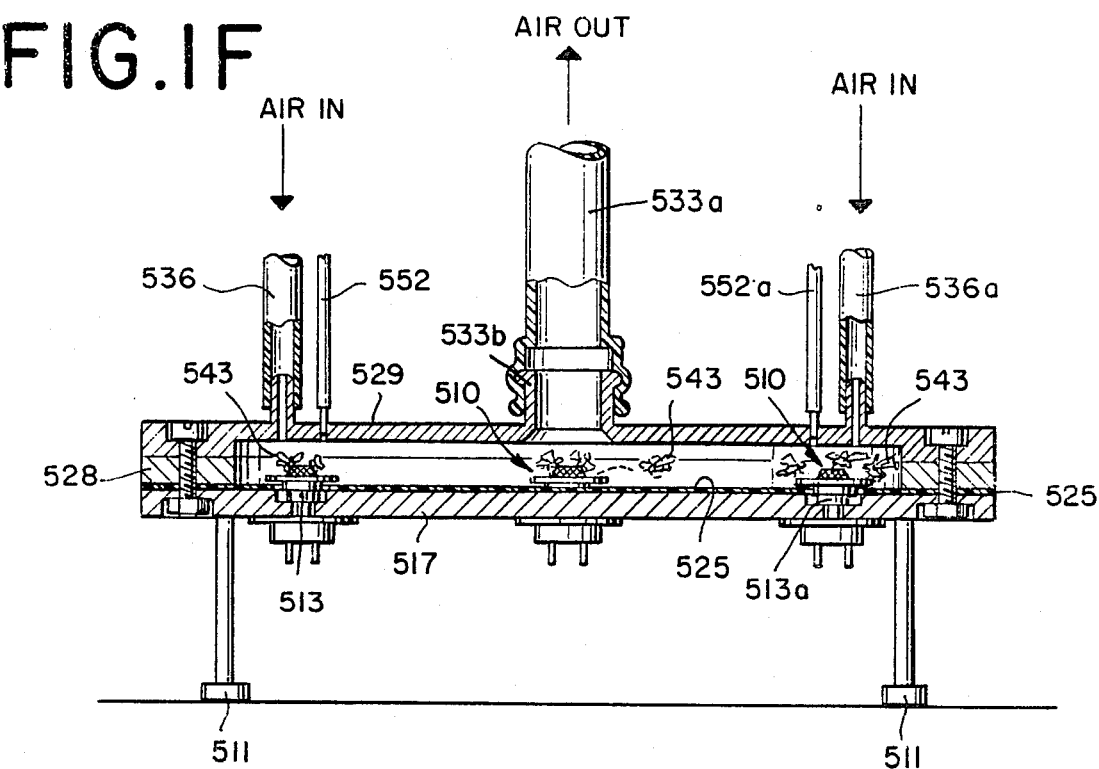
FIG.IF
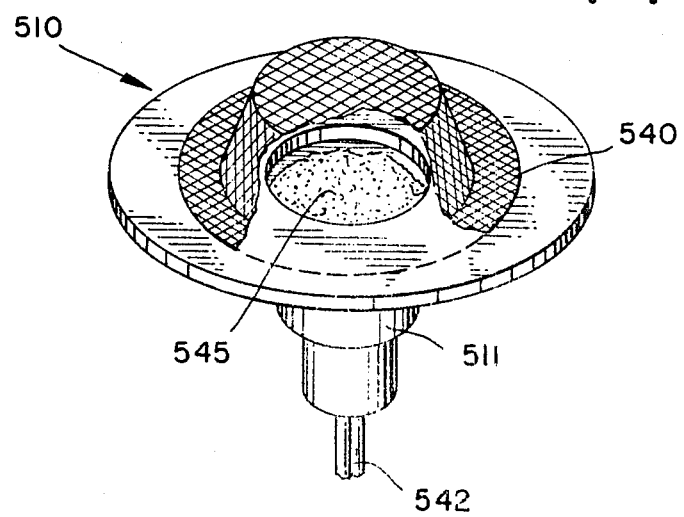
FIG.IG

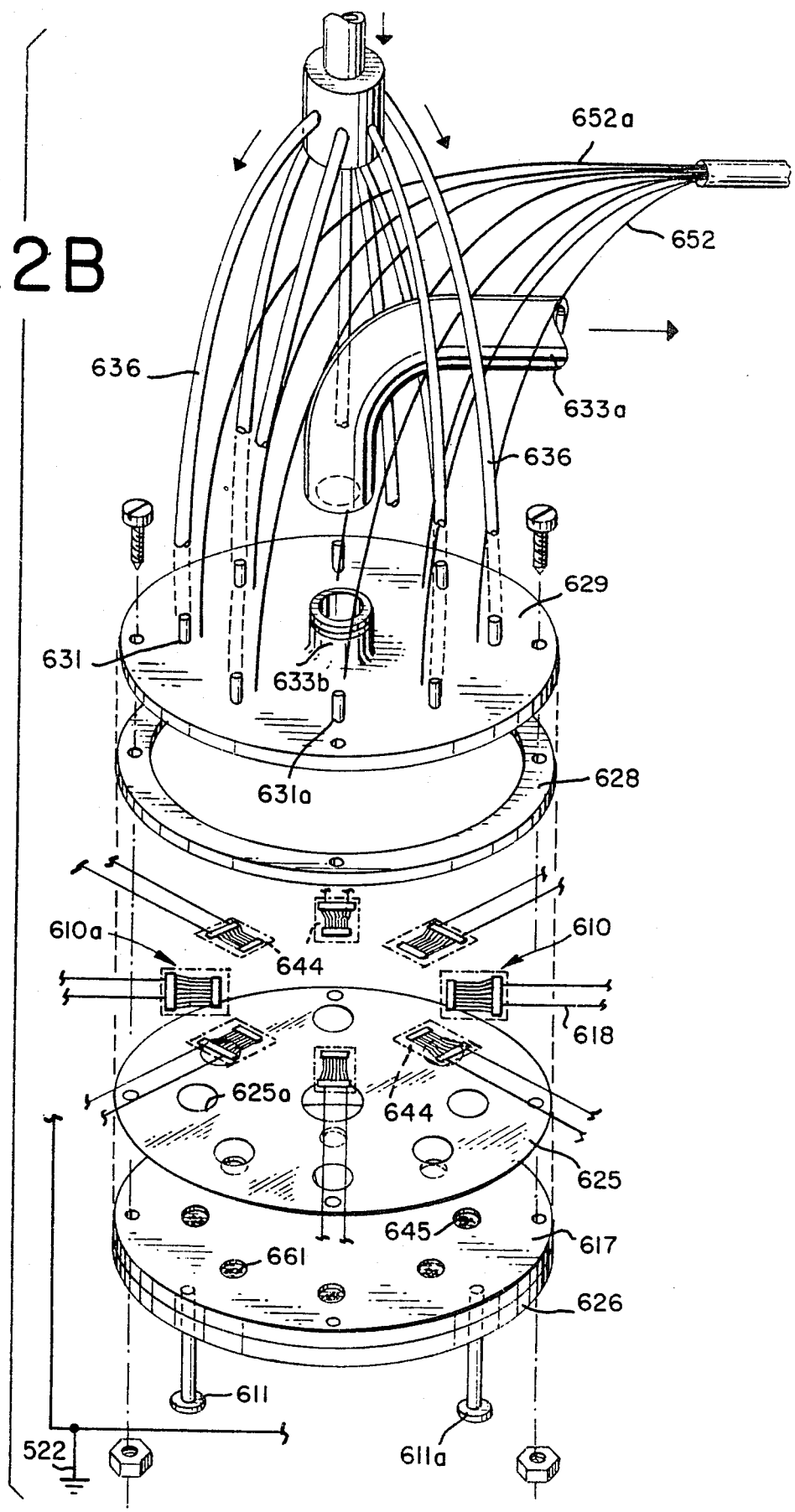

PROCESS FOR DETERMINATION OF REPELLENCY AND ATTRACTANCY

This application is a divisional of application for U.S. Pat. Ser. No. 002,023 filed on Jan. 9, 1987 which, in turn, is a continuation-in-part of application for U.S. Pat. Ser. No. 879,426 filed on June 27, 1986, now U.S. Pat. No. 4,693,890 issued on Sept. 15, 1987.

BACKGROUND OF THE INVENTION

This invention relates to the use of 1-nonen-3-ol as a repellent for house flies (*Musca domestica*) and further it relates to materials suitable for candle bodies which candle bodies include compositions of matter which are both (i) efficaciously insect repelling and (ii) perfuming in an aesthetically pleasing manner on use thereof. This invention also relates to apparatus useful in determining the repellency of molecules including said 1-nonen-3-ol comprising:
  (i) active and passive insect interest visual or electronic measuring and recording means which may, optionally, be connected to an electric power supply source;
  (ii) enclosed insect feeding and/or stimulating means having controlled limited access to the external environment surrounding said apparatus and associated with said measuring and recording means, said insect feeding and/or stimulating means being located at a fixed insect feeding and/or stimulating means location defined according to x, y and z coordinates having a defined first 3-space, said insect feeding and/or stimulating means consisting essentially of:
    (a) an insect feeding and/or stimulating surface which may, optionally, comprise at least two spaced electrically conductive elements
      (i) connected to said measuring and recording means; and
      (ii) capable of forming a complete circuit, said elements having such dimensions and spacing from one-another as to cause an attracted insect to complete a circuit of electron flow through or proximate to said elements;
    (b) immediately beneath said insect feeding and/or stimulating surface a composition of matter comprising molecules to be tested for attractancy and repellency;
    (c) immediately beneath said molecules to be tested, a feeding stimulant composition or a stimulant composition for said insects;
  (iii) optionally, steady-state direct lighting means for supplying a beam of direct light having a given substantially constant intensity or intensities and wavelength or wavelengths to said feeding and/or stimulating means location; and
  (iv) steady state air supply, air conduction and air removal means for supplying, conducting and removing air at a substantially constant mass flow rate and substantially constant linear velocity to, past and from a second 3-space immediately above said insect feeding and/or stimulating surface (simultaneously, if appropriate, with the supplying of the beam of direct light to said feeding and/or stimulating means location substantially immediately above said insect feeding and/or stimulating surface) said insect feeding and/or stimulating surface structure, optionally, being constructed so that said measuring and recording means is sensitive to the completion of a circuit of electron flow through or proximate said conductive elements of said insect feeding and/or stimulating surface, whereby the number and frequency of the insects attracted (if appropriate, relative to the attractancy of said direct lighting means) to the proximity of said feeding and/or stimulating means is capable of being determined either (a) using said measuring and recording means or (b) visually.

This invention also relates to a process using such apparatus for determining the repellency of molecules including said 1-nonen-3-ol.

Formulations exist in commerce which are said to provide adequate insect repellent properties, e.g., those set forth in U.S. Pat. No. 2,043,941 which indicate the repellency properties of methallyl disulfide having the structure:

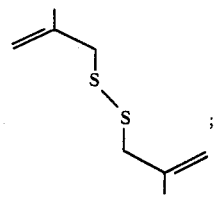

and those set forth in U.S. Pat. No. 4,449,987 issued on May 22, 1984 which indicate the combination of methyl heptenones, coumarin and indole for use in perfumed candles.

However, efficacious compositions of matter taken alone or for use in combination with perfumes for repelling house flies have not yet been developed.

Unsaturated alcohols and esters thereof are known with respect to controlling insects; however, they have been found to attract rather than repel such insects. Thus, U.S. Pat. No. 4,152,422 issued on May 1, 1979 sets forth 6-nonen-1-ol in a composition of matter used as an attractant for the male Mediterranean Fruit Fly. Chem. Abstracts Volume 103, No. 71086p concerns the synthesis of (Z)-8-dodecen-1-ol and its acetate as pheromone components of the Oriental Fruit Moth (*Grapholita molesta*). This is an abstract of the article in Acta Chem. Scan Ser. B., 1985, B39(4), pages 267–72. U.S. Pat. No. 4,364,931 issued on Dec. 21, 1982 discloses the use of 9(Z)-tetradecen-1-ol acetate in attracting male white-line dart moths.

Chem. Abstracts Volume 80, 1974, at No. 117098f discloses the use of trans-6-nonen-1-ol acetate as an ovipositional attractant and stimulant of the melon fly. U.S. Pat. No. 2,254,665 issued on Sep. 2, 1941, on the other hand, discloses the use of aliphatic alcohols in general in repelling insects which aliphatic alcohols have from 10 to 14 carbon atoms. Examples of the aliphatic alcohols of U.S. Pat. No. 2,254,665 are all saturated, to wit:
dodecyl alcohol;
octol alcohol;
hexadecyl alcohol;
tetradecyl alcohol; and
undecyl alcohol.

U.S. Pat. No. 2,254,665 fails to disclose the use of unsaturated alcohols in insect repellent compositions.

Chem. Abstracts Volume 74, 1971 at No. 99419f discloses various nonenyl acetates as attractants for female melon flies (abstract of *J. Med. Chem.*, 1971, 14(3), pages 236-9 including trans-2-nonen-1-yl acetate.

Formulations exist in commerce which are said to provide candle body materials that are both perfuming and insect repellent but such formulations have yielded a candle body that is either insufficiently insect repellent or aesthetically displeasing from an organoleptic standpoint.

When a candle burns, the heat of its flame melts a small pool of the candle body material around the base of the exposed portion of the wick, and this molten material is drawn up through the wick by capillary attraction to fuel the flame. Thus, the process that takes place in the burning of a candle imposes rather stringent functional requirements upon the candle body material.

The material of a candle body must be rigid enough to support itself and a relatively long wick filament, but it should not be excessively brittle at low temperatures. Its melting point is critical in that it should liquify temperatures, to which, it can be raised by radiant heat from the candle flame. If its melting temperature is too low, the candle will drip or, in an extreme case, the entire candle body will melt, dropping the wick into a pool of molten material with the hazardous possibility that the surface of the pool will ignite when this happens. If too high a temperature is required to melt the body material, the flame will be starved because insufficient fuel will be drawn up through the wick, with the result that the flame will be too small to maintain itself. When molten, moreover, the candle body material must have a relatively low viscosity in order to insure that it will be capable of being drawn up through the wick by capillary action.

In addition to meeting these requirements the candle body material must burn with a flame that is both luminous and smokeless and such odors as are produced by its combustion should not be unpleasant and should preferably be faint.

The functional requirements outlined above have, of course, been met by various candle body materials that are well known in the art, but heretofore no known materials that meet these requirements has been both:

(a) Perfuming to the environment surrounding the burning candle; and
(b) Adequately insect repellent to the environment surrounding the material at various environmental temperatures at atmospheric pressure, from a temperature of about 0° C. up to a temperature of about 50° C.

However, the desire for such a candle body material which is either transparent, opaque or translucent has long persisted where the candle composition is both insect repellent and perfuming on use.

An article by Burton, "Intrinsic mosquito repellency values of some chemical compounds" appearing in Volume 84, *American Perfumer and Cosmetics*, April 1969 at page 41, indicates that coumarin has a value of from 0.001 up to 0.003 micromoles per liter of air for 90% insect repulsion. It further states that indole has a property such that 0.004 up to 0.01 micromoles per liter of air of Indole are needed for 90% insect repulsion. On the other hand, the article by Burton indicates that a compound such as linalool requires 0.1 micromoles per liter of linalool per liter of air for 90% insect repulsion.

Nothing is stated in the Burton article which causes one to be taught that coumarin and indole taken in combination can be added to citronella oil or one or more methyl heptenones whereby the efficacy of the overall composition is maintained or increased and the overall concentration of insect repelling mixture is substantially diminished while at the same time causing an aesthetically pleasing aroma to be emanated from the burning candle on use.

Currently on the market are "citronella oil candles" containing approximately 1.5-3% citronella oil. On use these candles give off an essentially aesthetically displeasing aroma and are not quite effective in repelling insects as desired by the user.

U.S. Pat. No. 3,615,289 issued o Oct. 26, 1971 discloses candle compositions which may be transparent or pastel shaded which are adapted to incorporate perfumes without flashing during burning, and such compositions comprise as the basic components the mixture of (i) a thermoplastic polyamide resin formed from linoleic acid polymerized with a polyamine compound; (ii) an alkanol amide or alkanol amine; and (iii) a stearic acid compound. More specifically, U.S. Pat. No. 3,615,289 specifically discloses and claims a candle composition comprising about 15 to 35% by weight of a solid gel thermoplastic polymer which is a solid polyamide resin which is the soluble condensation product of an aliphatic dicarboxylic acid and an amine, the carboxyl and amino groups of adjacent mono units being condensed to an amide linkage in the polymer (and the resin may also be based on carboxylic and amine compounds having more than two carboxyl and amino groups respectively). At column 3, line 10 of U.S. Pat. No. 3,615,289 it is indicated that the candle contain about 0.4% by weight of a perfume material. Claim 3 at column 4 of U.S. Pat. No. 3,615,289 discloses a composition wherein 5 to 7% of the composition is replaced by a coumarin-indene copolymer resin. The insect repellency of compositions usable in U.S. Pat. No. 3,615,289 is not disclosed however.

U.S. Pat. No. 3,645,705 discloses a transparert candle body composition of matter which can contain:
(a) From about 35% up to about 85% by weight of an oil which is normally liquid at room temperature which may be light mineral oil and a natural oil;
(b) From about 7% up to 40% by weight of a long chain polyamide having a molecular weight between 6,000 and 9,000 and a softening point within the range of 185° C.–48° C. from about 7% up to about 30% by weight of an alcohol which may be a $C_8$ up to a $C_{12}$ primary alcohol.

At column 3, line 56 of U.S. Pat. No. 3,645,705 it is disclosed that an odor masking agent may be incorporated into the candle composition. Generally this disclosure is set forth at lines 30–44 of U.S. Pat. No. 3,645,705 thusly:

"The inclusion in the composition of certain alcohols that produce otherwise desirable properties may result in a material that burns with an acrid or pungent odor. In such cases a small amount of an odor masking agent can be incorporated in the composition. The material sold by Fritzche, Dodge and Olcott as its No. 41984 has been found satisfactory when incorporated in the composition in amounts up to about 0.2 percent by weight. The odor-masking agent is desirable when less expensive alcohols are used and may be unnecessary if the alcohols are highly refined, but from the standpoint of cost, the use of the cheaper alcohols and an odor-masking agent is indicated and produces satisfactory results. If desired, a small amount of perfume can be added to the composition to complete the odor-masking effect."

Nothing in U.S. Pat. No. 3,645,705, however, discloses the applicability to the composition disclosed therein of insect repellent materials. Nothing discloses the use of a composition of matter in U.S. Pat. No. 3,645,705 which will be both a perfumant and an insect repellent.

U.S. Pat. No. 4,051,159 issued on Sept. 27, 1977 discloses a "shaped, self-supporting transparent fragrance emitting article comprising a high percentage of a thermoplastic polyamide resin having substantially uniformly dispersed therein a $C_{14}$–$C_{22}$ alkyl alcohol and a fragrance emitting material". U.S. Pat. No. 4,051,159 however, does not indicate that the compositions of matter disclosed therein are useful for the purposes of candles and particularly are useful for fragrant candles or insect repellent candles or candles which are both fragrance emitting and insect repellent.

Published Japanese patent application No. J57088-101 assigned to the Agency of Industrial Sci. Tech. of Japan discloses the use of benzal acetone, laevo-carvone and thymol as insect repelling materials contained in conjunction with an aromatic substance, silica gel, talc or a binder such as polyvinyl alcohol or carboxymethyl cellulose.

Published Japanese patent application No. J 57088-101 however, does not indicate that compositions of matter are useful for the purposes of candles and particularly, are useful for fragrant candles or insect repellent candles which are both fragrancy emitting and insect repellent in an efficacious manner. The abstract of published Japanese patent application No. J 57088-101 is as follows:

"Insect repellent contains benzalacetone (I) as active component. (I) has an immediate effect used in combination with sublimating substance such as naphthalene and camphor. The ratio of blend of benzalacetone to the sublimating substance is 90:1–5:95. Optionally, an excipient such as silica gel, talc and binder such as PVA or CMC and aromatic substance can be added (I) can be put in a suitable vessel, can be prepared as as tablet, or can be supported on cloth or paper.

Benzalacetone has the melting point of 41°–42° C. and the boiling point of 260°–262° C. The saturated gas concentration of benzalacetone is 0.045 mg/1 by gas chromatography and is one tenth that of laevo-carvone and one third that of thymol, and therefore it has long-lasting effect.

(I) is nontoxic to warm-blooded animals, and shows repelling effect for a long period of time. It is prepared in low cost, and can be stored in a plastic vessel, since it does not etch plastics. It is particularly effective in the repellin of insects for clothes, e.g., *Tinea pellionella.*"

Furthermore, both humans and animals are annoyed by insects and this problem is so acute as to render certain regions essentially uninhabitable by man. Disregarding the annoyance, insect bites are often accompanied by profound and in some cases serious physiological effects. Many diseases, particularly those of tropical origin, are transmitted by means of insect bites. In spite of man's constant warfare against insects they still occur in large numbers and they continue to plague both man and animals. Insecticide chemists have devoted considerable time and effort to this problem. Thousands of compounds have been tested for their toxic effect upon insects. These compounds either act as stomach poisons or respiratory paralyzers and are effective in a number of instances.

Another approach to the problem, which has also been given considerable thought, is the development of substances which have a repellent effect upon the insects. These substances can be applied upon the host in a variety of manners and serve to prevent attacks by insects which under normal conditions are attracted to these individuals.

Toxicity and repellency are not usually correlated, and it does not follow that a substance toxic to the insect is in any way repellent to it. On the other hand materials that are repellent to insects are not generally toxic and in a number of cases effective repellents are actually harmless to insects.

In order to be effective for this purpose the substance must of course, possess a high degree of repellency. In addition they must not be toxic or harmful to the individual treated. In general, it is believed that repellents are irritating to the sensory mechanism of the insect. It does not follow that a substance possessing this sensory irritating effect upon insects has a similar effect upon humans or animals. In a number of instances substances which definitely repel insects are pleasing to man and substances repugnant to man are attractive to insects.

Nothing in the prior art, however, discloses the use of 1-nonen-3-ol having the structure:

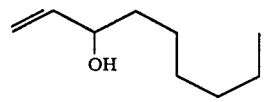

in repelling house flies (*Musca domestica*) or even infers that 1-nonen-3-ol has the highly efficacious ability to repel house flies (*Musca domestica*), and nothing in the prior art discloses olfactometry apparatus useful in measuring such aforesaid properties.

Indeed, the literature teaches away from our invention as exemplified in "Materials Tested as Insect Attractants" compiled by M. Berazo and N. Green in Agriculture Handbook No. 239 in Table 2 wherein it is stated that 3-methyl-1-nonen-3-ol (a homologue of 1-nonen-3-ol) has on a scale of 1 to 3 an attractancy of "1" for the Oriental Fruit Fly and an attractancy of "1" for the Mediterrean Fruit Fly and 4,8-dimethyl-7-nonen-4-ol has on a scale of 1 to 3 an attractancy of "2" for the Oriental Fruit Fly and an attractancy of "3" for the Mediterrean Fruit Fly and an attractancy of "1" for the Mexican Fruit Fly and an attractancy of "1" for *Drosophila*. With respect to any of the nonenol derivatives set forth therein the USDA Agriculture Handbook 239 indicates that the nonenol derivatives are neither attractants nor repellents for house flies (that is *Musca domestica*).

Various prior art techniques for studying feeding habits of insects have been found useful in formulating processes and apparatus for determining relative attractancy and repellency for insects. Thus, the paper "Laboratory Blood Feeding of *Culicoides mississippiensis* (Diptera:Ceratopogonidae) Through A Reinforced Silicone Membrane" by Davis, Butler, Roberts, Reinert and Kline (J. Med. Entomol. Vol 20, No. 2: 177–182) discloses the preparation and use of a durable silicone membrane for feeding *Culicoides mississippiensis* in the laboratory. Further, the paper entitled "IN VITRO Feeding of Ornithodoros Ticks For Rearing And Assessment of Disease Transmission", Butler, Hess, Endris and Holscher, ACAROLOGY VI, Volume 2, published 1984 by Ellis Horwood Limited, Market Cross House, Cooper Street, Chichester, West Sussex, PO 19 1EB, England discloses the advantages of feeding of haematophagous arthropods through artificial membranes. A number of preferred embodiments of our invention includes the use of the teachings of the aforementioned papers. Accordingly, the aforementioned papers are incorporated herein by reference.

BRIEF DESCRIPTION OF THE DRAWINGS

FIG. 1A is a representation of one of the landing pad sections on plate 517 of the apparatus of FIG. 1 (a transducer mechanism) where the house flies (*Musca domestica*) land if and when they are attracted by the substance being tested, e.g., 1-nonen-3-ol.

FIG. 1B is a schematic diagram (blown up for illustration purposes) of an embodiment of the operational portion of the olfactometer apparatus of FIG. 1, useful in ascertaining the inter alia the efficacy of the 1-nonen-3-ol as a repellent for house flies (*Musca domestica*) but not including the utilization of the computer-assisted efficacy measuring apparatus.

FIG. 1C is a schematic diagram of the embodiment of the olfactometer apparatus of FIG. 1 (not blown up) useful in ascertaining the efficacy of the 1-nonen-3-ol, inter alia, as a repellent for house flies (*Musca domestica*) indicating in schematic block flow diagram form the utilization of computer-assisted efficacy measuring apparatus.

FIG. 1F is a cut-away side elevation view of the base portion of the apparatus of FIG. 1, also illustrated in FIG. 1D, wherein the air hose 533a is connected to the remainder of the apparatus and the insects 543 have been de-anaesthitized.

FIG. 1G is a cut-away perspective view of an insect landing pad 510 as shown in FIG. 1, without any insects thereon.

FIG. 2B is a schematic diagram (exploded for illustration purposes) of the operational section of the embodiment of the olfactometer apparatus of FIG. 2A useful in ascertaining the efficacy of the 1-nonen-3-ol, inter alia, as a repellent for house flies (*Musca domestica*) but not indicating the diagram of the computer-assisted efficacy measuring apparatus associated therewith as shown in FIG. 2A.

FIG. 4A is another top view of the lower section of the olfactometer apparatus of FIG. 2D looking down at base plate 625 and at heating coils 660 and 660a indicating in schematic block flow diagram form heat transfer and forced fluid flow apparatus.

FIG. 5A is an unexploded view of a cross-sectional portion of FIG 5.

SUMMARY OF THE INVENTION

Figure 1:
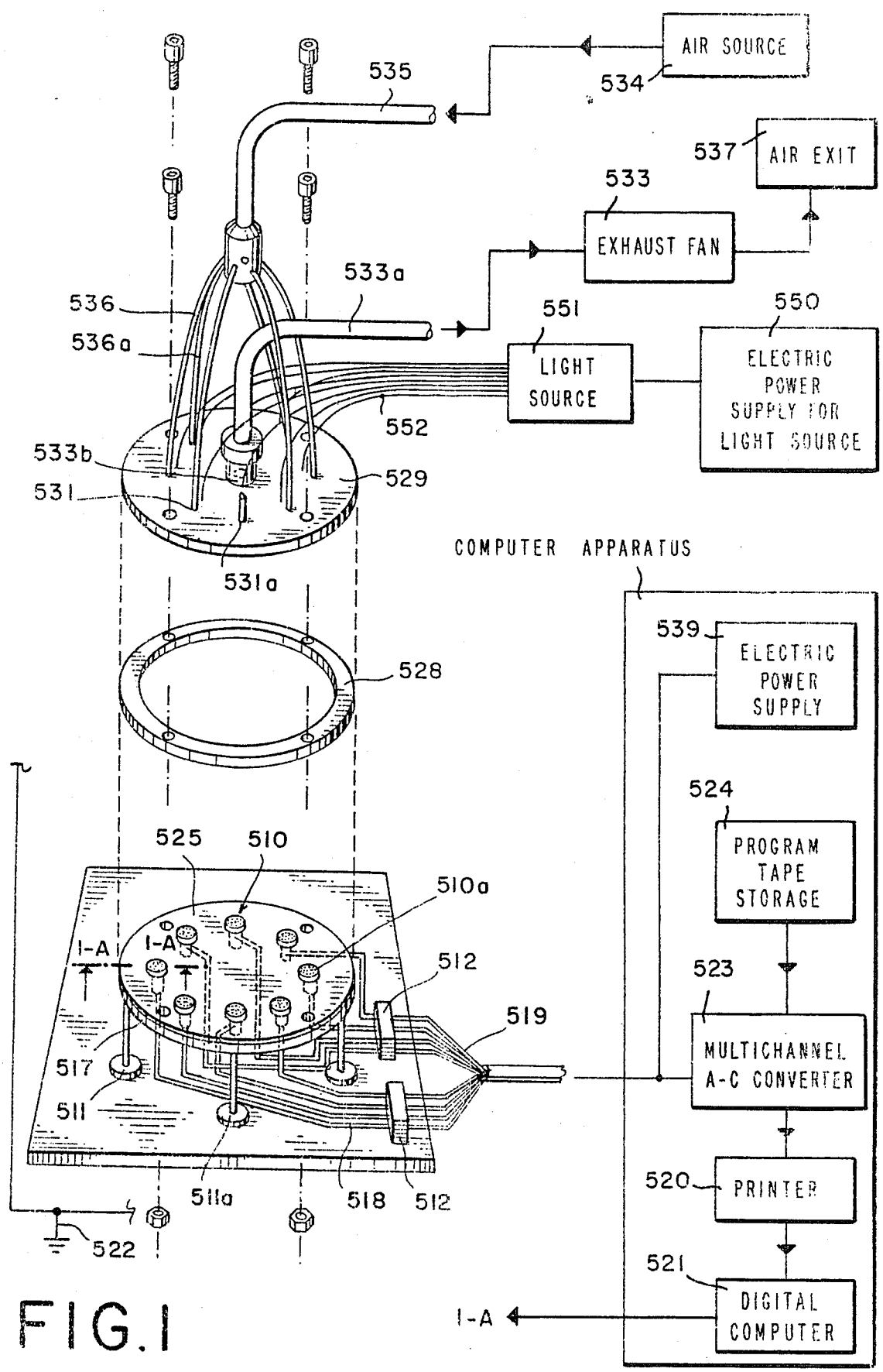
FIG. 1 is a schematic diagram (blown up for illustration purposes) of an embodiment of the olfactometer apparatus useful, inter alia, in ascertaining the efficacy of the 1-nonen-3-ol as a repellent for house flies (*Musca domestica*) indicating in schematic block flow diagram form the utilization of computer-assisted efficacy measuring apparatus.

Our invention is directed to the utilization of 1-nonen-3-ol per se and incorporated into a polymer body or candle body as a house fly (*Musca domestica*) repellent.

Our invention is also directed to apparatus for testing insect repellency and attractancy of such molecules as 1-nonen-3-ol comprising:

(i) active and passive insect interest visual or electronic measuring and recording means which may, optionally, be connected to an electric power supply source;

(ii) enclosed insect feeding and/or stimulating means having controlled limited access to the external environment surrounding said apparatus and associated with said measuring and recording means, said insect feeding and/or stimulating means being located at a fixed insect feeding and/or stimulating means location defined according to x, y and z coordinates in a defined first 3-space, said insect feeding and/or stimulating means consisting essentially of:

(a) an insect feeding and/or stimulating surface which may, optionally, comprise at least two spaced electrically conductive elements:
(1) connected to said measuring and recording means; and
(2) capable of forming a complete circuit, said elements having such dimensions and spacing from one another as to cause an attracted insect to complete a circuit of electron flow through or proximate to said elements;

(b) immediately beneath said insect feeding and/or stimulating surface a composition of matter comprising the molecules to be tested for attractancy and repellency;

(c) immediately beneath said molecules to be tested, a feeding stimulant composition or a stimulant composition for said insects;

(iii) optionally, steady state direct lighting means for supplying a beam of direct light having a given substantially constant intensity and wavelength or wavelengths to said feeding and/or stimulating means location; and (iv) steady state air supply, air conduction and air removal means for supplying, conducting and removing air at a substantially constant mass flow rate and substantially constant linear velocity to, past and from a second 3-space immediately above said insect feeding and/or stimulating surface (and, in the event that a steady-state direct lighting means is used, simultaneously with the supplying of said beam of direct light to said feeding and/or stimulating means location) substantially immediately above said insect feeding and/or stimulating surface, said insect feeding and/or stimulating surface structure optionally being constructed so that said measuring and recording means is sensitive to the completion of a circuit of electron flow through or proximate said conductive elements of said insect feeding and/or stimulating surface, whereby the number and frequency of the insects attracted to the proximity of said feeding and/or stimulating means is capable of being determined either (a) using said measuring and recording means or (b) visually.

The apparatus of our invention may be juxtaposed in an upright position as set forth in FIGS. 1-3 and 5 described in detail, infra, or it may be juxtaposed in an inverted or substantially inverted position.

Our invention also relates to a process for testing insect repellency and attractancy of molecules using such apparatus as set forth, supra, by means of first providing such apparatus and then:
(i) anaesthetizing selected insects at a location apart from the feeding and/or stimulating means means in the apparatus;
(ii) then supplying one or more anaesthetized insects to said first defined 3-space in the apparatus;
(iii) then enclosing said first 3-space surrounding said feeding and/or stimulating means whereby access thereto is limited to the air supply, air conduction and air removal means of the apparatus;
(iv) (optionally) then forming an electrical circuit connection between said measuring and recording means and said feeding and/or stimulating means;
(v) then supplying, conducting and removing air at a substantially constant mass flow rate and substantially constant linear velocity to, past and from said second defined 3-space; then
(vi) simultaneously supplying direct light (optionally) to said second defined 3-space, the optional supplying of light and the supplying of air being carried out at such conditions and for such a period of time that the anaesthetized insects are de-anaesthetized and recommence life activities; and
(vii) then observing either (a) on said measuring and recording means or (b) visually, the number and frequency of de-anaesthetized insects attracted to the surface or proximity of said feeding and/or stimulating means.

A second testing technique concerns the electrophysiological study of the neural corrolates of attraction and repulsion in *Musca domestica* L. (Diptera:Muscidae) (house flies). Different points in the house fly olfactory neuroarchitecture were studied using electrophysiology in an effort to identify the neural corrolates of attractant and repellent signals resulting from potentially attractant and repellent substances.

Recordings from the antennal lobe of the deuterocerebrum of the *Musca domestica* L. (Diptera:Muscidae) showed that the repellent signals were highly distinguishable from the attractant signals. Signals from repellents (e.g., 1-nonen-3-ol) showed a shift in base line potential of approximately 25 m Volts whereas attractant signals showed no shift.

Thus, neural signals of the antennal lobe are used herein as an assay for olfactory canvassing to predict behavioral activity of the *Musca domestica* L. (Diptera:Muscidae) (house fly).

By the same token, neural signals of the antennal base, the funiculus and the antennal nerve are used herein as an assay for olfactory canvassing to predict behavioral activity of the *Musca domestica* L. (Diptera:Muscidae)(house fly).

Another aspect of our invention relates to the formation of 1-nonen-3-ol repelling articles, that is, articles useful for the repellent of house flies (*Musca domestica*) in combination with compatible polymers, e.g., high density polyethylene or low density polyethylene. Thus, one aspect of the invention provides a process for forming 1-nonen-3-ol-containing polymeric particles such as foamed polymeric pellets which include a relatively high concentration of 1-nonen-3-ol.

Thus, one aspect of our invention relates to the formation of 1-nonen-3-ol polymeric pellets by means of introduction into a single screw or twin screw extruder of, in series, thermoplastic polymer followed by 1-nonen-3-ol which is compatible with the thermoplastic polymer, in turn, (optionally) followed by introduction of a gaseous blowing agent or blowing agent which will produce a gas which is inert to the polymer and to the 1-nonen-3-ol previously introduced into the extruder.

The advantageous of using a foamed polymeric particle are multiple, to wit: improved handling, greater retention of 1-nonen-3-ol when not in use; greater length of time during which release of 1-nonen-3-ol from the polymer is at "steady state" or "zero order".

The nature of the extruder utilized in the process of our invention to form the polymeric 1-nonen-3-ol-containing polymer particles of our invention may be either single screw or double screw. Thus, the types of extruder that can be used are disclosed at pages 246–267 and 332–349 of the Modern Plastic Encyclopedia, 1982–1983, published by the McGraw-Hill Publishing Company, the disclosure of which is incorporated by reference herein. More specifically, examples of extruders which are usable in carrying out one of the processes of our invention (with modification for introduction of the 1-nonen-3-ol) downstream from introduction of the polymer and with further modification that the gaseous blowing agent is introduced still further downstream from the point of introduction of the 1-nonen-3-ol are as follows:

1. The Welex "Super Twinch" 3.5" extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kans. 67277;
3. Modified Sterling model 4000 and 5000 series extruder manufactured by Sterling Extruder Corporation of 901 Durham Avenue, South Plainfield, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder manufactured by the Werner & Pfleiderer Corporation of 663 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff single screw, twin screw, or foam extrusion equipment manufactured by Berstorff Corporation, P.0. Box 240357, 8200-A Arrowridge Blvd., Charlotte, N.C. 28224.

In producing the 1-nonen-3-ol polymer particles of our invention various polymers may be utilized, for example, low density polyethylene high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ethylene and vinyl acetate. Preferred co-polymers are ethylene vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed by the E. I. duPont de Nemours Company under the tradename "ELVAX ®" and by the Arco Polymer Division under the trademark "DYLAND ®" and by the Exxon Corporation of Linden, N.J. under the trademark "DEXXON ®". Ethylene/ethyl acrylate co-polymers are marketed by Union Carbide Corporation under the tradename "EEA RESINS ®".

The polymer is added to the single screw or twin screw extruder at a feed rate in the range of from about 80 up to about 300 pounds per hour while maintaining the temperature of the screw extruder between about 160° and about 240° C. If the polymer or co-polymer powder is added to the extruder at a reference "barrel segment", then the 1-nonen-3-ol is added to the extruder under pressure downstream from the addition point of the polymer at 1 or more of "barrel segments" S-2, S-3, S-4, S-5, S-6, S-7, S-8 or S-9 (referring to FIG. 7 briefly described, supra and described in detail, infra.

The proportion of 1-nonen-3-ol to resin can vary from small but effective amounts on the order of about 1% of the weight of resin body up to about 45% by weight of the resin body. In general it is preferred to use between about 5% up to about 30% based on the weight of the resin body of 1-nonen-3-ol. This is an optimum amount balancing the proportion of 1-nonen-3-ol against the time period over which the article emits the 1-nonen-3-ol and against the tendency of the 1-nonen-3-ol to "oil out". This "oiling out" is specifically avoided as a result of use of the foaming agent discussed, infra.

Various polymers are useful in the practice of our invention. Specific examples of polymers useful in the practice of our invention are as follows:

(a) DYLAN ® brand of low density polyethylene DYLAN ® is a trademark owned by the Atlantic Richfield Company of Los Angeles, Calif.;

(b) DYLITE ® of expandable polystryene compositions. DYLITE ® is a trademark of the Atlantic Richfield Company of Los Angeles, Calif.;

(c) SUPER DYLAN ® a high density polyethylene. SUPER DYLAN ® is a trademark of the Atlantic Richfield Company of Los Angeles, Calif.;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated by reference herein;

(f) Polyene/alpha-olefin as exemplified and disclosed in U.S. Pat. No. 4,369,291, the specification for which is incorporated by reference herein;

(g) Poly-alpha-olefins as exemplified in Canadian Letters Pat. No. 1,137,069 issued on Dec. 7, 1982, the specification for which is incorporated by reference herein;

(h) Polymeric compositions as disclosed in Canadian Letters Pat. No. 1,137,068 issued on Dec. 7, 1982, the specification for which is incorporated by reference herein;

(i) Poly-alpha-olefins disclosed in Canadian Letters Pat. No. 1,137,067, the specification for which is incorporated by reference herein;

(j) Polyolefins described in Canadian Letters Pat. No. 1,137,066, the specification for which is incorporated by reference herein;

(k) Polyethylene oxides as disclosed in Canadian Letters Pat. No. 1,137,065 issued on Dec. 7, 1982, the specification for which is incorporated by reference herein;

(l) Olefin polymers and co-polymers as disclosed in Canadian Letters Pat. No. 1,139,737, the disclosure of which is incorporated by reference herein. Canadian Pat. No. 1,139,737 was issued on Jan. 18, 1983;

(m) Polyolefins disclosed in Canadian Letters Pat. No. 1,139,738, the disclosure of which is incorporated by reference herein. Canadian Pat. No. 1,139,738 was issued on Jan. 18, 1983;

(n) Chlorinated PVC as disclosed in *Polymer* 1982, 23 (7,Suppl.), 1051-6 abstracted at Chem. Abstracts 97: 145570y, 1982;

(o) Polyepsilon caprolactone co-polymers made by means of alcohol initiated polymerization as disclosed in *J. Polym. Sci.* Polym. Chem. Ed. 1982, 20(2), pages 319–26, abstracted at chem. Abstracts, Volume 96: 123625x, 1982;

(p) Styrene acrylonitrile co-polymers as disclosed in Diss. Abstracts, Int. B, 1982, 42(8), 3346 and abstracted at Chem. Abstracts 96: 143750n (1982);

(q) Co-polymers of epsilon caprolactone with 1,4-butane diol as disclosed at Kauch. Rezine, 1982, (2), 8–9, abstracted at Chem. Abstracts, Volume 96: 182506g (1982);

(r) Polyesters as disclosed in U.S. Pat. No. 4,326,010, the specification for which is incorporated by reference herein;

(s) Chlorinated polyethylene as disclosed by Belorgey, et al., *J. Polym. Sci.* Polym. Phys. Ed. 1982, 20(2), 191–203;

(t) Plasticized polyepsilon caprolactone co-polymers containing dimethyl phthalate plasticizers as set forth in Japanese Pat. No. J81/147844, abstracted at Chem. Abstracts, Volume 96: 69984y (1982), the specification for which is incorporated by reference herein;

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

Downstream from the addition point of the 1-nonen-3-ol, optionally, the gaseous or liquid containing blowing agent may be added (e.g., at barrel segments S-5, S-6, S-7, S-8, S-9 or S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed 1-nonen-3-ol-containing particle.

The feed rate range of 1-nonen-3-ol may be between about 0.5% up to about 45% by weight of the polymer.

The die of the extruder may create rod, sheet, film or ribbon. The resulting product may then, if desired, be pelletized to form 1-nonen-3-ol-containing polymer particles or the ribbon may be used "as-is" as an 1-nonen-3-ol-containing polymeric article of manufacture itself.

In addition to the optional gaseous blowing agents (which are necessarily "inert" gases), blowing agents may be added at the same point on the extruder which will create gaseous voids in the 1-nonen-3-ol-containing polymer articles of our invention and these "blowing agents" are well known to one having ordinary skill in the art. Examples of such non-gaseous containing materials which yield gases on admixture with the polymer in the extruder but which are still inert to the insect attractant are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, lines 1–5, the specification for which is incorporated by reference herein;

(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specifications for which are incorporated herein by reference; and (iv) Azo bis(formamide); diazoaminobenzene; N,N'-dinitrosopentamethylene tetramine; N,N'-dimethyl-N,N'-dinitrosoterephthalamide; p,p'-oxy-bis(-benzene sulfonyl semicarbazide); azo bis-(isobutyronitrile); p,p'-oxy-bis(benzene sulfonyl hydrazide); p,p'-diphenyl-bis(sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be for example injection molded to form a useful article. Such injection molding can be carried out in accordance with the procedure as set forth in U.S. Pat. No. 3,268,636 issued on Aug. 23, 1966, the specificaiton for which is incorporated oy reference herein.

In addition, our invention relates to candle body materials which on use are both insect repellent and perfuming in which contain 1-nonen-3-ol in order to repel house flies (*Musca domestica*).

The resulting extruded (and if desired pelletized) material may then be for example injection molded to form a useful article. Such injection molding can be carried out in accordance with the procedure as set forth in U.S. Pat. No. 3,268,636 issued on Aug. 23, 1966, the specificaiton for which is incorporated by reference herein.

In addition, our invention relates to candle body materials which on use are both insect repellent and perfuming in which contain 1-nonen-3-ol in order to repel house flies (*Musca domestica*).

The house fly repellent-perfuming compositions which form part of the candle body materials are within the following specifications:

(I) from 5 up to 100% by weight of an efficacious perfuming/insect repellent composition consisting essentially of 1-nonen-3-ol; and (II) from 0 up to 95% by weight of a standard perfuming substance (non-insect repellent) which may be one or a combination of the following materials:
the methyl ester of 2,5-dihydroxy-4,6-dimethyl benzoic acid;
dihydro myrcenol;
oakmoss absolute;
benzyl acetate;
geraniol;
isobornyl acetate;
citronellyl acetate;
para-t-butyl phenyl isovaleraldehyde;
benzyl salicylate;
hexyl cinnamic aldehyde;
geranonitrile;
patchouli oil;
alpha-terpineol;
tetrahydromuguol;
phenyl ethyl alcohol;
cedrenal;
methyl ionone;
cinnamyl acetate;
benyzl benzoate;
L-Citronellal;
nerol;
geranyl formate;
geranyl acetate;
eugenol;
alpha Farnesene;
beta Farnesene;
citral;
n-Nonanal;
n-Octanal; and
trans,trans delta-damascone.

The foregoing formula may require a solubilizing agent, e.g., the methyl ester of dihydroabietic acid (commercial name: HERCOLYN D ®, benzyl benzoate, isopropyl myristate and/or $C_{12}$–$C_{14}$ isoparaffin hydrocarbons.

The candle base composition can be standard paraffin wax, or it can be transparent or pastel shaded as more particularly described in U.S. Pat. No. 3,615,289 issued on Oct. 26, 1971 (the disclosure of which is incorporated by reference herein) and wherein the candle body comprises as the basic components a mixture of:

(i) a thermoplastic polyamide resin formed from linoleic acid polymerized with a polyamine compound;
(ii) an alkanol amide or alkanol amine; and
(iii) a stearic acid compound.

The weight of ratio of candle body: 1-nonen-3-ol/perfumant substance of our invention may vary from about 0.8% up to about 10% with a range of from about 0.8% up to about 2.0% being preferred when no non-insect repelling perfume oil is used in conjunction with the 1-nonen-3-ol; and with a range of from about 1.5% up to about 10% by weight of the overall composition being preferred when a non-insect repelling perfume oil is used in conjunction with the 1-nonen-3-ol.

Specifically, the polyamide may be a "Versamid" resin which is a thermoplastic condensation product of polymerized linoleic acid with various polyamine compounds such as ethylene diamine, ethylene triamine and the like. Specific "Versamid" compounds are "VERSAMID ®900", "VERSAMID ®930, "VERSAMID ®940, "VERSAMID ®948, "VERSAMID ®950" and "VERSAMID ®1635". These compounds are products of the Henkel Chemical Corporation of Minneapolis, Minn.

Another substance required in the clear candle composition consists of about 20–55% by weight of an alkanol amine or alkanol amide prepared by the reaction of a fatty acid ester and amine whereby the ester and the amine are in substantially equal proportions, for example, compounds such as Barlol 12C2 (manufactured by the Barrid Chemical Company) a monoalkyl diethanolamine have 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. These stearic acid compounds serve as stabilizing agents which permit the ready incorporation of the insect repellent/perfumant compositions of our invention up to a level of approximately 5% (total proportion of perfume oil-insect repellent composition). They are carriers for the perfumant/insect repellent and may be used in a proportion of between 1 and 50% by weight of the composition although the preferable range is between 20 to 30%. In this connection it is possible to use up to about 10% by weight of perfumant/insect repellent if part of the formula is replaced by the material "Nevex 100", a product which is a coumarin-indene copolymer resin of very little unsaturation, manufactured by the Neville Chemical Company.

Rather than being a crystalline paraffin wax the candle base of our invention may be an oil gel that has as its base a light mineral oil, an inexpensive natural oil or a combination of such oils which oil gel has a non-greasy surface and feel and sufficient rigidity to be self-supporting at room temperatures. Such a gel is disclosed in U.S. Pat. No. 3,645,705 issued on Feb. 29, 1972, the disclosure of which is incorporated by reference herein. Such compositions of matter include:
(a) from about 35% up to about 85% by weight of an oil which is normally liquid at room temperature chosen from the group consisting of light mineral oil and natural oils having iodine values substantially within the range of 40–135;
(b) from about 7% up to about 40% by weight of a long chain polyamide having a molecular weight substantially within the range of 6000–9000 and a softening point substantially within the range of 18° C.–48° C.; and
(c) from about 7% to about 30% of an alcohol selected from the group consisting of 8 to 12 carbon primary alcohols.

Such composition may additionally include from about 1% up to about 15% of a methyl ester; up to about 5% by weight of stearic acid and up to about 5% by weight of an oxidation inhibiting agent and up to about 5% by weight of an acid selected from the group consisting of dimer and trimer acids.

Table I, set forth below, sets forth the results of the utilization of the olfactometer apparatus of FIG. 1 described in detail in the "Detailed Description of the Drawings" section, infra.

In this table the following abbreviated terms are used:
ACT.: Strikes at landing pad (Reference Numeral 110a in FIG. 1 and FIG. 1A).
TOT (%): Percent of total strikes per run.
(%)ACT-BLK: Percent activity excluding blank.
(%)ACT-POS.C: Percent activity minus percent of positive control.
FACTOR (ACT/CON): Ratio of activity divided by activity of positive control.

TABLE I

| ACT | TOTAL (%) | (%) ACT − BLK. | (%) ACT − POS.C | FACTOR (ACT/CONT) |
|---|---|---|---|---|
| 348.0 | 9.500000 | 10.500000 | −7.500000 | 0.600000 |
| 286.0 | 6.100000 | 6.700000 | −11.500000 | 0.400000 |
| 3.0 | 1.600000 | 1.900000 | −16.500000 | 0.100000 |
| 15.0 | 1.300000 | 1.500000 | −18.600000 | 0.100000 |
| 7.0 | 1.200000 | 1.500000 | −12.500000 | 0.100000 |
| 1.0 | 0.700000 | 0.700000 | −10.400000 | 0.100000 |
| 2.0 | 0.500000 | 0.600000 | −24.000000 | 0.000000 |
| 1.0 | 0.200000 | 0.200000 | −20.100000 | 0.000000 |
| 6.0 | 0.100000 | 0.300000 | −72.200000 | 0.000000 |
| 0.0 | 0.000000 | 0.000000 | −2.800000 | 0.000000 |
| 0.0 | 0.000000 | 0.000000 | −20.100000 | 0.000000 |
| 55.0 | 2.000000 | 2.300000 | −16.200000 | 0.100000 |
| 117.0 | 3.500000 | 4.200000 | −17.900000 | 0.200000 |
| 90.0 | 5.000000 | 5.900000 | −14.200000 | 0.300000 |
| 22.0 | 2.400000 | 2.900000 | −19.800000 | 0.100000 |
| 2.0 | 1.100000 | 1.400000 | −36.400000 | 0.000000 |
| 6.0 | 0.800000 | 1.000000 | −10.700000 | 0.100000 |
| 42.0 | 4.600000 | 4.900000 | −15.000000 | 0.200000 |
| 1.0 | 0.100000 | 0.200000 | −5.500000 | 0.000000 |
| 7.0 | 0.900000 | 1.000000 | −14.000000 | 0.100000 |
| 1.0 | 0.100000 | 0.100000 | −18.300000 | 0.000000 |
| 253.0 | 3.700000 | 4.000000 | −11.000000 | 0.300000 |
| 161.0 | 5.200000 | 5.400000 | −10.200000 | 0.300000 |
| 88.0 | 3.600000 | 4.000000 | −10.100000 | 0.300000 |
| 3.0 | 0.700000 | 0.800000 | −5.300000 | 0.100000 |
| 15.0 | 1.100000 | 1.400000 | −21.200000 | 0.100000 |
| 7.0 | 1.500000 | 1.700000 | −20.900000 | 0.100000 |
| 17.0 | 2.200000 | 2.300000 | −14.900000 | 0.100000 |
| 972.0 | 7.600000 | 8.300000 | −3.100000 | 0.700000 |
| 69.0 | 2.200000 | 2.700000 | −22.300000 | 0.100000 |
| 47.0 | 2.200000 | 2.500000 | −13.200000 | 0.200000 |
| 1.0 | 0.500000 | 0.500000 | −25.900000 | 0.000000 |
| 30.0 | 2.200000 | 2.500000 | −11.900000 | 0.200000 |
| 345.0 | 7.200000 | 7.800000 | −4.600000 | 0.600000 |
| 498.0 | 9.900000 | 10.700000 | 1.000000 | 1.100000 |
| 128.0 | 4.500000 | 5.200000 | −6.300000 | 0.500000 |
| 4.0 | 0.700000 | 0.900000 | −13.400000 | 0.100000 |
| 39.0 | 1.500000 | 1.800000 | −12.700000 | 0.100000 |
| 3.0 | 0.700000 | 0.800000 | −19.000000 | 0.000000 |
| 18.0 | 2.500000 | 2.700000 | −18.700000 | 0.100000 |
| 14.0 | 1.500000 | 1.800000 | −15.500000 | 0.100000 |
| 2.0 | 0.400000 | 0.500000 | −14.900000 | 0.000000 |
| 4.0 | 0.100000 | 0.500000 | −12.100000 | 0.000000 |
| 2.0 | 0.100000 | 0.100000 | −11.600000 | 0.000000 |
| 0.0 | 0.000000 | 0.000000 | −18.400000 | 0.000000 |
| 2.0 | 0.300000 | 0.300000 | −7.700000 | 0.000000 |
| 0.0 | 0.000000 | 0.000000 | −9.800000 | 0.000000 |
| 165.0 | 4.300000 | 4.800000 | −7.400000 | 0.400000 |
| 90.0 | 4.958678 | 5.859375 | −14.192708 | 0.292208 |
| 117.0 | 3.506143 | 4.195052 | −17.891717 | 0.189935 |

TABLE I-continued

| ACT | TOTAL (%) | (%) ACT − BLK. | (%) ACT − POS.C | FACTOR (ACT/CONT) |
|---|---|---|---|---|
| 22.0 | 2.404372 | 2.910053 | −19.841270 | 0.127907 |
| 2.0 | 1.149425 | 1.398601 | −36.363636 | 0.037037 |
| 42.0 | 4.590164 | 4.918033 | −14.988290 | 0.247059 |
| 55.0 | 2.027772 | 2.344416 | −16.197783 | 0.126437 |
| 6.0 | 0.757576 | 1.020408 | −10.714286 | 0.086957 |
| 7.0 | 0.909091 | 0.980392 | −14.005602 | 0.065421 |
| 1.0 | 0.147710 | 0.172117 | −5.507745 | 0.030303 |
| 161.0 | 5.193548 | 5.444707 | −10.246872 | 0.346983 |
| 88.0 | 3.594771 | 4.003640 | −10.054595 | 0.284790 |
| 253.0 | 3.675189 | 3.979865 | −10.964291 | 0.266316 |
| 3.0 | 0.721154 | 0.835655 | −5.292479 | 0.136364 |
| 1.0 | 0.108696 | 0.118624 | −18.268090 | 0.006452 |
| 30.0 | 2.186589 | 2.544529 | −11.874470 | 0.176471 |
| 47.0 | 2.231719 | 2.460733 | −13.193717 | 0.157191 |
| 17.0 | 2.245707 | 2.254642 | −14.854111 | 0.131783 |
| 69.0 | 2.238806 | 2.690058 | −22.261209 | 0.107813 |
| 7.0 | 1.461378 | 1.745636 | −20.947631 | 0.076923 |
| 15.0 | 1.110289 | 1.353791 | −21.209386 | 0.060000 |
| 498.0 | 9.910448 | 10.650128 | 1.005133 | 1.104213 |
| 972.0 | 7.565969 | 8.265306 | −3.129252 | 0.725373 |
| 345.0 | 7.205514 | 7.830232 | −4.630050 | 0.628415 |
| 128.0 | 4.537398 | 5.192698 | −6.328600 | 0.450704 |
| 1.0 | 0.469484 | 0.471698 | −25.943396 | 0.017857 |
| 18.0 | 2.486188 | 2.714932 | −18.702866 | 0.126761 |
| 39.0 | 1.542722 | 1.806392 | −12.737378 | 0.124204 |
| 14.0 | 1.545254 | 1.822917 | −15.494792 | 0.105263 |
| 4.0 | 0.744879 | 0.881057 | −13.436123 | 0.061538 |
| 3.0 | 0.650759 | 0.802139 | −18.983957 | 0.040541 |
| 2.0 | 0.267380 | 0.322061 | −7.729469 | 0.040000 |
| 2.0 | 0.415800 | 0.530504 | −14.854111 | 0.034483 |
| 4.0 | 0.143318 | 0.164813 | −12.072518 | 0.013468 |
| 2.0 | 0.086580 | 0.097561 | −11.560976 | 0.008368 |
| 0.0 | 0.000000 | 0.000000 | −9.796984 | 0.000000 |
| 1.0 | 0.735294 | 0.740741 | −10.370370 | 0.666667 |
| 15.0 | 1.270110 | 1.492537 | −18.606965 | 0.074257 |
| 348.0 | 9.451385 | 10.507246 | −7.487923 | 0.583893 |
| 3.0 | 1.612903 | 1.898734 | −16.455696 | 0.103448 |
| 0.0 | 0.000000 | 0.000000 | −20.149254 | 0.000000 |
| 7.0 | 1.151316 | 1.508621 | −12.500000 | 0.107692 |
| 2.0 | 0.478469 | 0.558659 | −24.022346 | 0.022727 |
| 1.0 | 0.199601 | 0.218341 | −20.087336 | 0.010753 |
| 0.0 | 0.000000 | 0.000000 | −2.800000 | 0.000000 |
| 286.0 | 6.143931 | 6.657356 | −11.499069 | 0.366667 |
| 6.0 | 0.148112 | 0.254022 | −72.226926 | 0.003505 |

DETAILED DESCRIPTION OF THE DRAWINGS

FIG. 1 is an exploded view of a first embodiment of the olfactometer apparatus used in testing the efficacy of, for example, 1-nonen-3-ol as a house fly (*Musca domestica*) attracting material. Air source 534 feeds air through line 535 through air distributors 536, 536a et seq. onto base plate 517 containing insect landing sites 510, 510a, et seq. The base plate 517 is separated from the spacer plate 529 for the air lines 536 whereby the air lines 536 are held in place at positions 531, 531a et seq. using spacer ring 528. Air exits through line 533a using exhaust fan 533.

The air exit is indicated by reference numeral 537.

Simultaneously with the supplying of air from air source 534, light is supplied through light guides 552, 552a et seq. from light source 551 which is powered by electric power supply 550. An example of such light guide is marketed by RADIO SHACK ® Division of Tandy Corporation of Fort Worth, Tex. 76102 under the trademark ARCHER ® Catalog No. 276-228 ("1.0 mm optical plastic fiber length 5 meters"). An example of light source 551 is KRATOS Monochromatic Illuminator GM 100 Miniture VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. Another light supply source is the KRATOS GM 200 Double Grating Monochromator. Another example of a useful light source is the KRATOS GM 252 High Intensity Grating Monochromator. The base plate 517 is also separated from the spacer plate 529 for the light guides 552 whereby the light guides 552, 552a et seq. are held in place also at positions 531, 531a et seq. In the first embodiment illustrated in FIG. 1 as well as in FIGS. 1B, 1C, 1D and 1F, spacer ring 528 separates plate 529 which holds the air line 536 and the light guide 552 in place from plate 517 on which landing pads 510 are located.

The olfactometer of FIG. 1 is assisted with computer apparatus shown in schematic form and block flow diagram form using reference numerals 520, 521, 523, 524 and 539. Dampers 511a, 511b et seq. hold base plate 517 in place horizontally. When an insect lands on landing sites 510, 510a et seq. the landing is recorded electrically through a sensor shown in magnified form in FIG. 1A. The sensor which is, in fact, a transducer 513 causes an electrical impulse caused by the pressure of the insects landing to proceed through wire 518 and then through wire 519 (held in position by holder 512) to a multi-channel A-D converter 523 (using electric power supply 539). Converter 523 is associated with program tape storage 524, printer 520 and data link to digital computer 521. Thus, a recording of the data as set forth in Table I, supra, is effected. Reference numeral 522 represents a "Faraday Cage" completing the olfactometer circuit.

FIG. 1A is a partial cross section view taken along lines 1A—1A of FIG. 1 showing one specific landing site 510 having a surface on which the insect lands if attracted by such a material as 1-nonen-3-ol or does not land if repelled by such a material as 1-nonen-3-ol which is also located at other specific landing sites. At other landing sites nothing is located (and these are the "control" landing sites). The olfactometer may include base plate 526 (shown in FIG. 1B) covered by face plate 517. The base plate 526 in turn is located on dampers 511a, 511b, et seq. Face plate 517 remains covered with such a material as SARAN WRAP ® 525 (shown in FIG. 1B) which fits snugly under the landing pad 510 et seq. so that any insects that are attracted to the landing sites 510 are not distracted to any other areas on base plate 517.

FIG. 1B is an enlarged exploded view of that portion of the olfactometer apparatus which involves the provision of light and air to the insect landing sites 510, 510a, 510b et seq. particularly showing how face plate 517 is mounted on base plate 526.

FIG. 1C shows the apparatus of FIG. 1A connected and ready for use in its testing mode where spacer plate 529 is connected in a tightly fitting manner to ring 528 which, in turn, is connected in a tightly fitting manner to face plate 517 and face plate 517 is connected in a tightly fitting manner to base plate 526.

Figure 1D:
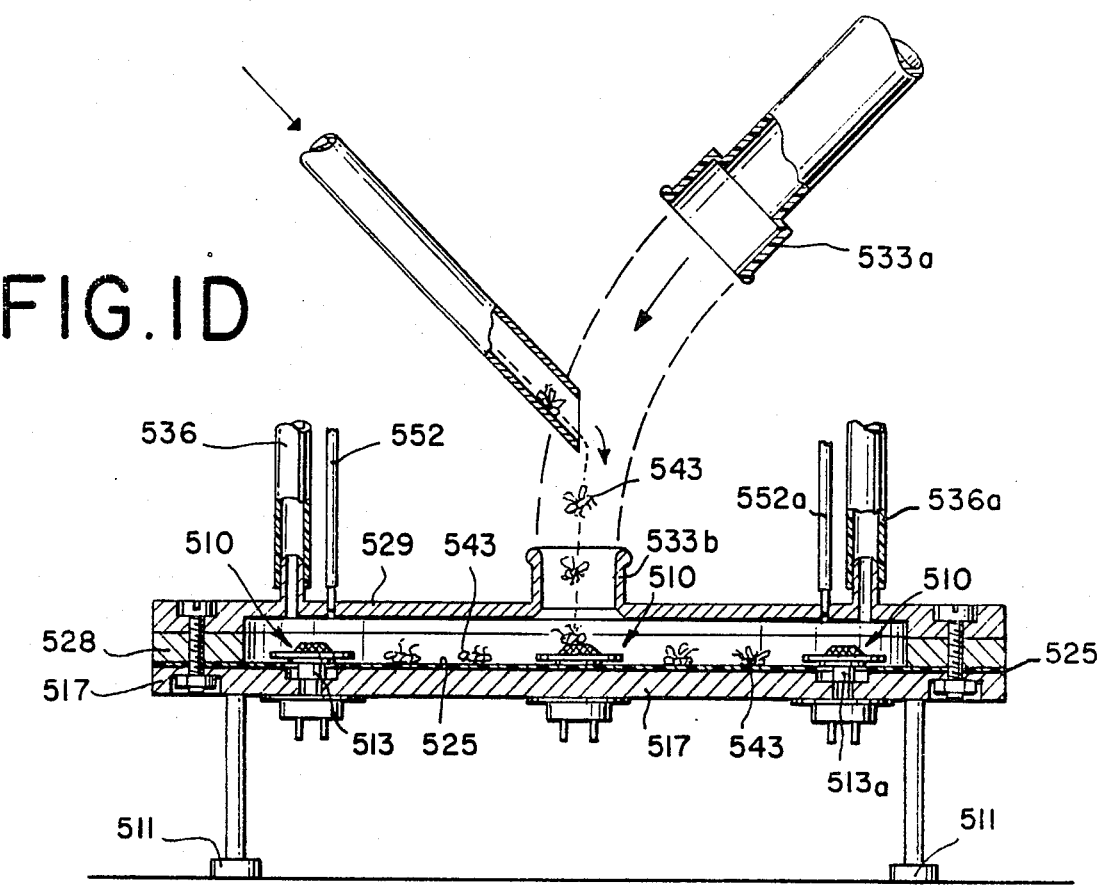
FIG. 1D is a cut-away side elevation view of the base section of the olfactometer apparatus of FIG. 1 with the air hose 533 disconnected in order to load the apparatus with $CO_2$-anaesthitized insects prior to using the apparatus of FIG. 1 in order to test the attractancy or repellency of certain molecules for the said insects.
Figure 1E:
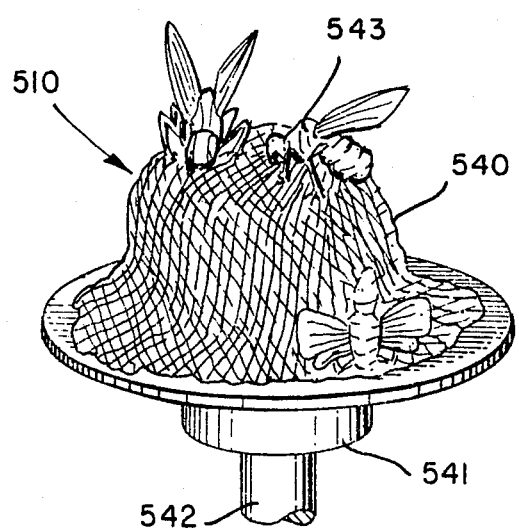
FIG. 1E is a perspective diagram of an embodiment of an insect landing pad section useful in operating the apparatus of FIG. 1 (landing pad 510) with insects 543 feeding thereon.

FIG. 1D is a cut-away side elevation view of the olfactometer apparatus of FIG. 1 being prepared for use with air hose 533a removed from air connector base 533b so that anaesthetized insects 543, e.g., anaesthetized *Musca domestica* may be placed on plate 517 prior to the testing procedure which involves the connection of air hose 533a to joint 533b. It should be noted that after the air hose 533a is connected and air is fed in through lines 536 and light is transported through light guides 552 the insects 543, 543a et seq. are de-anaesthetized and may or may not be attracted to landing sites 510, 510a et seq. as shown in detail in FIG. 1E. The landing pads are composed of a screen device ("hat") 540 underneath which is an insect attractancy or repellency source 545 (shown in FIG. 1G). The landing pad in FIG. 1D is supported by support 541 connected through shaft 542 to wire 518 which, in turn, is connected to the computer-assisted date collection and recordal mechanism.

FIG. 1F shows the olfactometer section concerning the operational part of the olfactometer in place and in operation with insects 543 attracted to pad 540 on pad 540.

FIG. 1G is a cut-away perspective view of landing pad 540 wherein the screen device which supports any attracted insects is located on support 510; and insect attractancy or repellency source 545 is shown under the screen.

FIGS. 2A, 2B, 2C and 2D are exploded views of a second embodiment of the olfactometer apparatus of our invention used in testing, inter alia, the efficacy of 1-nonen-3-ol as house fly (*Musca domestica*) attracting materials. Air source 634 feeds air through line 635 through air distributors 636, 636a et seq. onto base plate 617 containing insect landing sites 610, 610a et seq. The landing sites 610 and 610a are shown in detail in FIGS. 2F, 2G, 2J and 2K. The base plate 617 is separated from the spacer plate 629 for the air lines 636 whereby the air lines 636 are held in place at positions 631, 631a et seq. Air exits through line 633a using exhaust fan 633.

Simultaneously with the air being fed through lines 636, 636a et seq. from air source 634, light is guided through light guides 652 and 652a exemplified, infra, using light source 651 powered by electric power source 650. The base plate 617 is separated from the spacer plate 629 also for the light guides 652, 652a et seq. whereby the light guides 652, 652a et seq. are held in place at positions 631, 631a et seq.

The olfactometer is assisted with computer apparatus shown in schematic form and block flow diagram form using reference numerals 620, 621, 623, 624 and 639. Dampers 611a, 611b et seq. hold base plate 617 in place horizontally.

When an insect 643 is de-anaesthetized and in action in 3-space 646 in an area defined according to x, y and z coordinates), e.g., a house fly (*Musca domestica*)(shown in FIG. 2E) lands on a sensor landing site, the landing is recorded electrically through the sensor 610, 610a et seq. shown in magnified form in FIGS. 2F, 2G, 2J and 2K. The sensor 610, 610a et seq. causes an electrical impulse to proceed through wire 618 and then through wire 619 (using electric power source 639) to a multichannel A-D converter 623 which is associated with program tape storage 624, printer 620 and digital computer associated with modem and main frame 621. Reference numeral 622 indicates the completion of the circuit for the olfactometer as a "Faraday Cage". Spacer ring 628 separates spacer plate 629 from the face plate 617. The spacer ring 628 (when the olfactometer is ready to use) is held sealably in place on the sensor devices 610 as a result of the inclusion of silicone seals 649 which are located on each of the sensors and are also located on base plate 617. The silicone seals are shown in detail by reference numeral 649 on FIG. 2F. In the embodiment of the olfactometer of our invention shown in FIGS. 2A, 2B, 2C and 2D, spacer 628 is fitted onto the silicone seals 649 which are located not only on sensors 610 but also on face plate 617. Preferably, face plate 617 is mounted on base plate 626 which may, if desired, contain a cavity 657 for a fluid heating coil (as illustrated in FIG. 3, 4 and FIG. 4A).

Figure 2A:
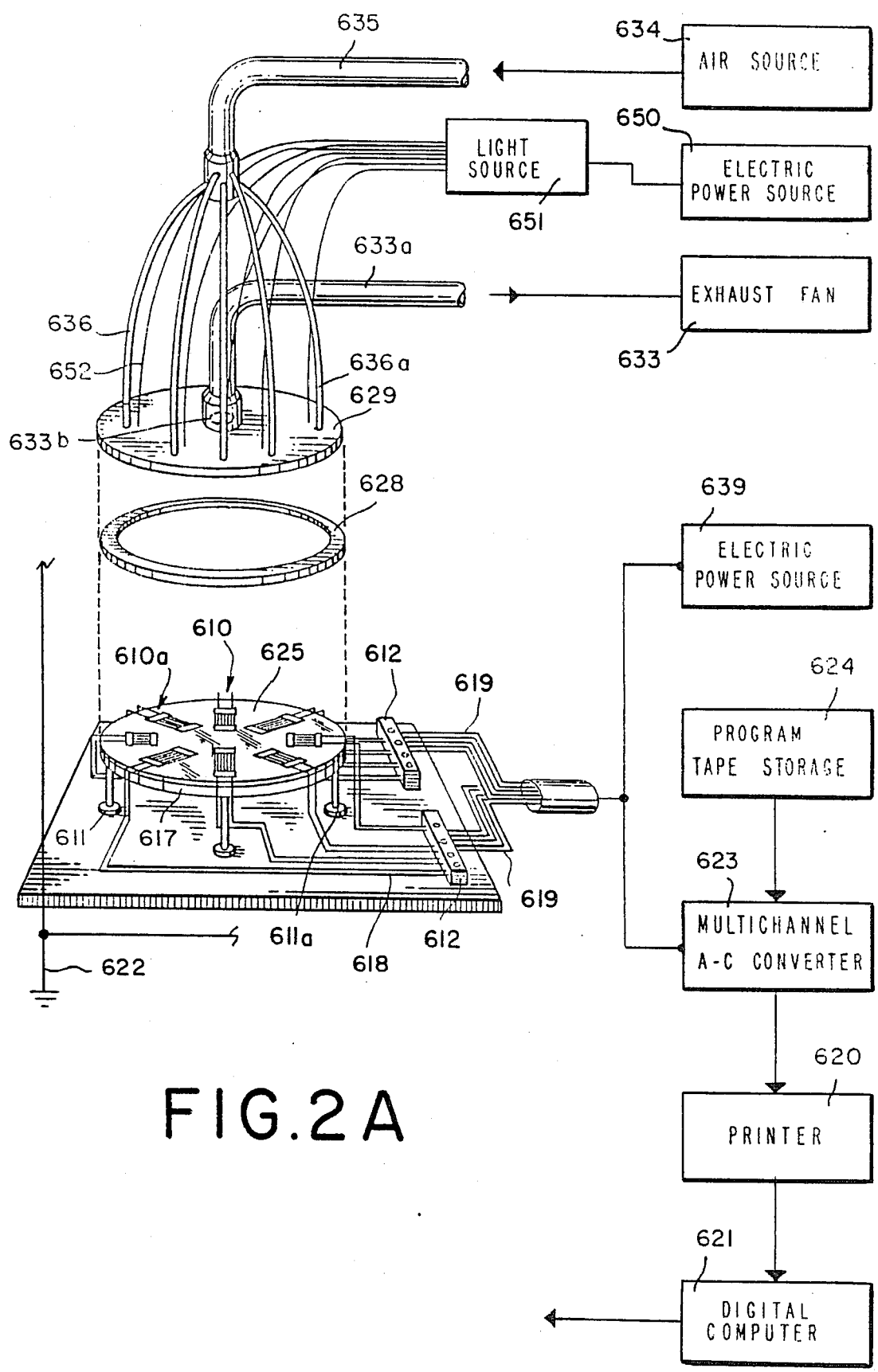
FIG. 2A is a schematic diagram (exploded for illustration purposes) of a secod embodiment of the olfactometer apparatus useful, inter alia, in ascertaining the efficacy of the 1-nonen-3-ol as a repellent for house flies (*Musca domestica*) indicating in schematic block flow diagram form the utilization of computer-assisted efficacy measuring apparatus.
Figure 2C:
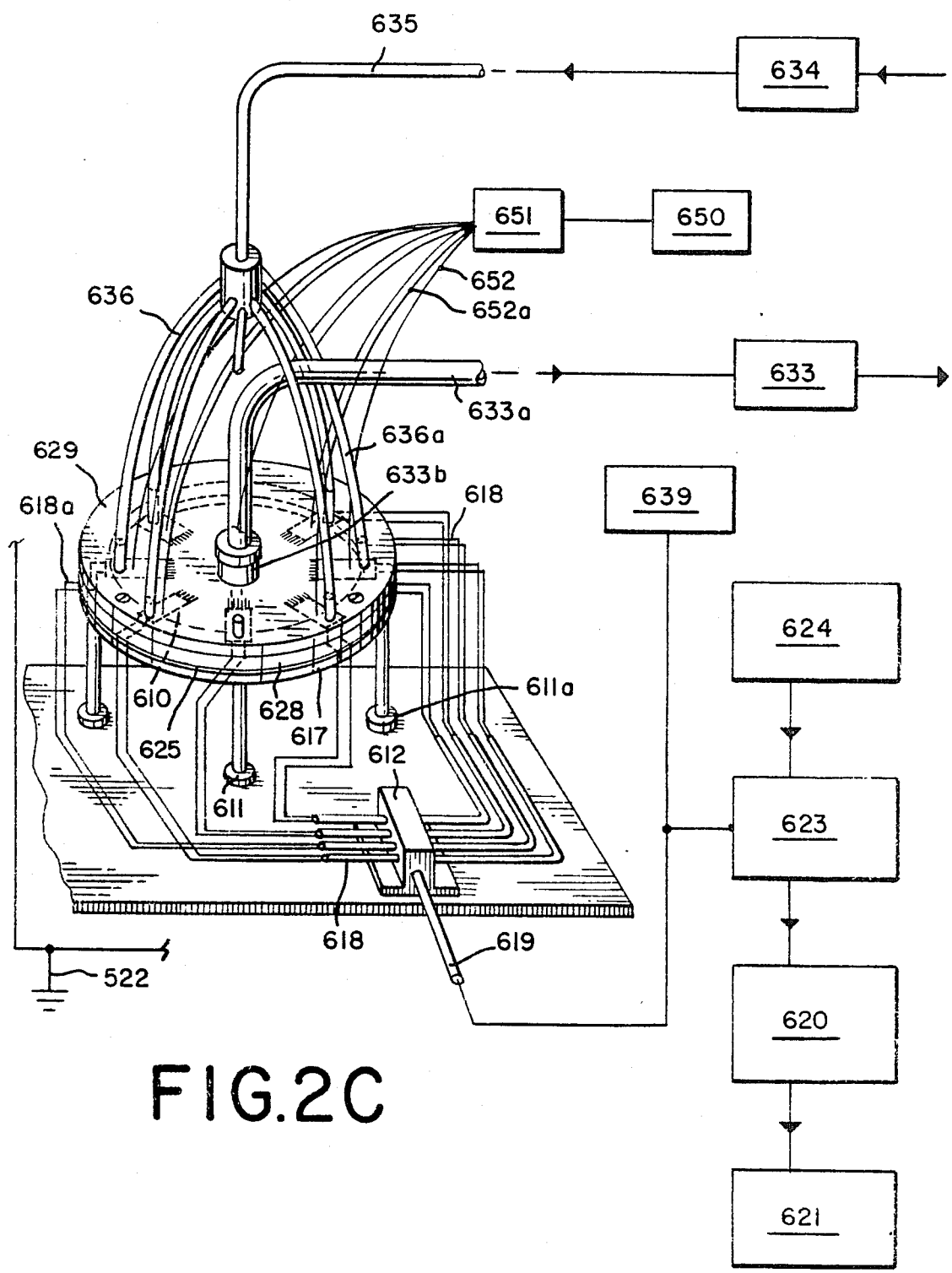
FIG. 2C is a schematic diagram of the embodiment of the olfactometer apparatus of FIG. 2A (shown ready for operation) useful, inter alia, in ascertaining the efficacy of the 1-nonen-3-ol as a repellent for house flies (*Musca domestica*) indicating in schematic block flow diagram form the utilization of computer-assisted efficacy measuring apparatus.
Figure 2D:
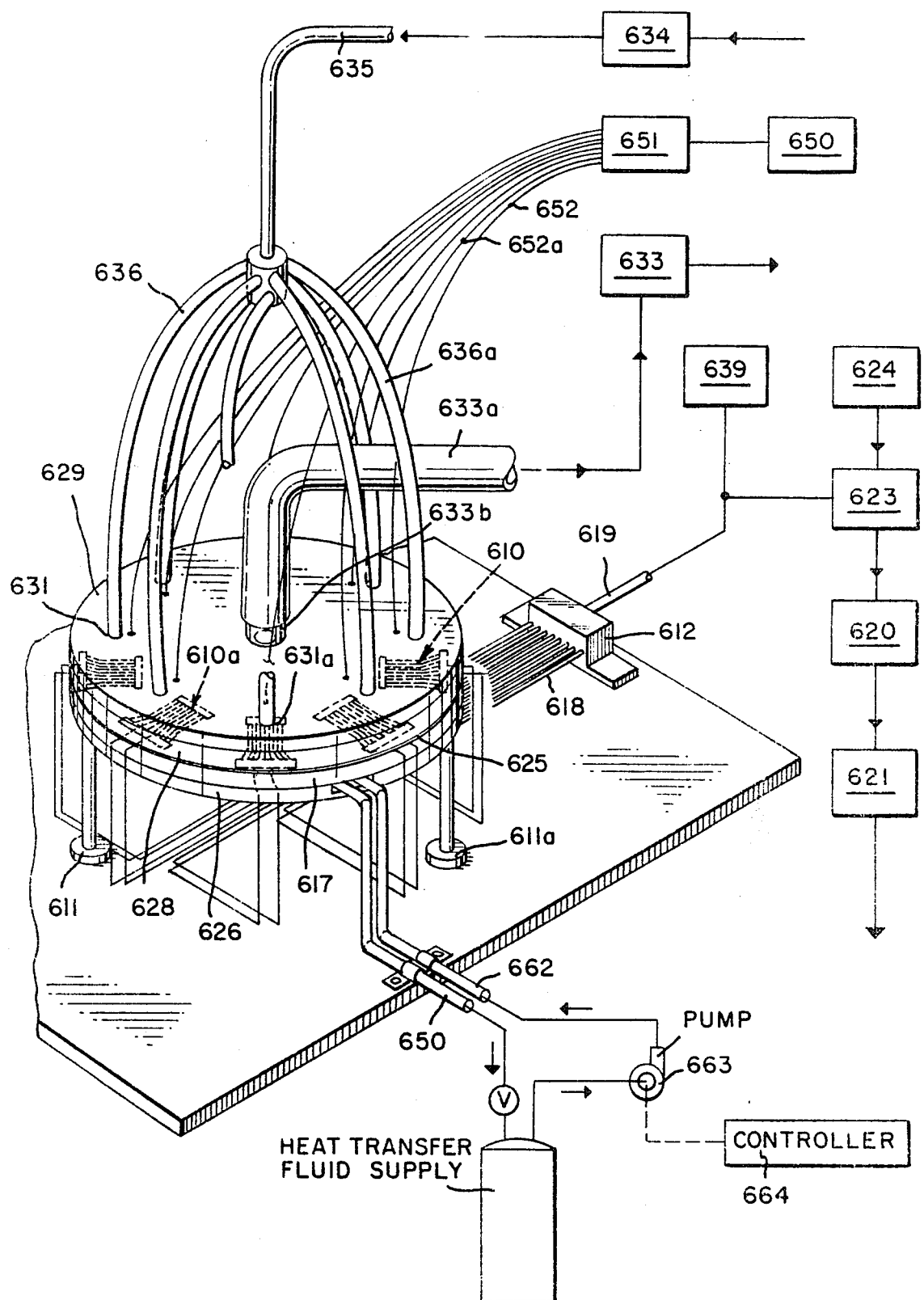
FIG. 2D is a schematic diagram of a third embodiment of the olfactometer apparatus of our invention (ready for operation) useful in ascertaining the efficacy, inter alia, of the 1-nonen-3-ol as a repellent for house flies (*Musca domestica*), and also indicating in schematic block flow diagram form the utilization of computer-assisted efficacy measuring apparatus.
Figure 2E:
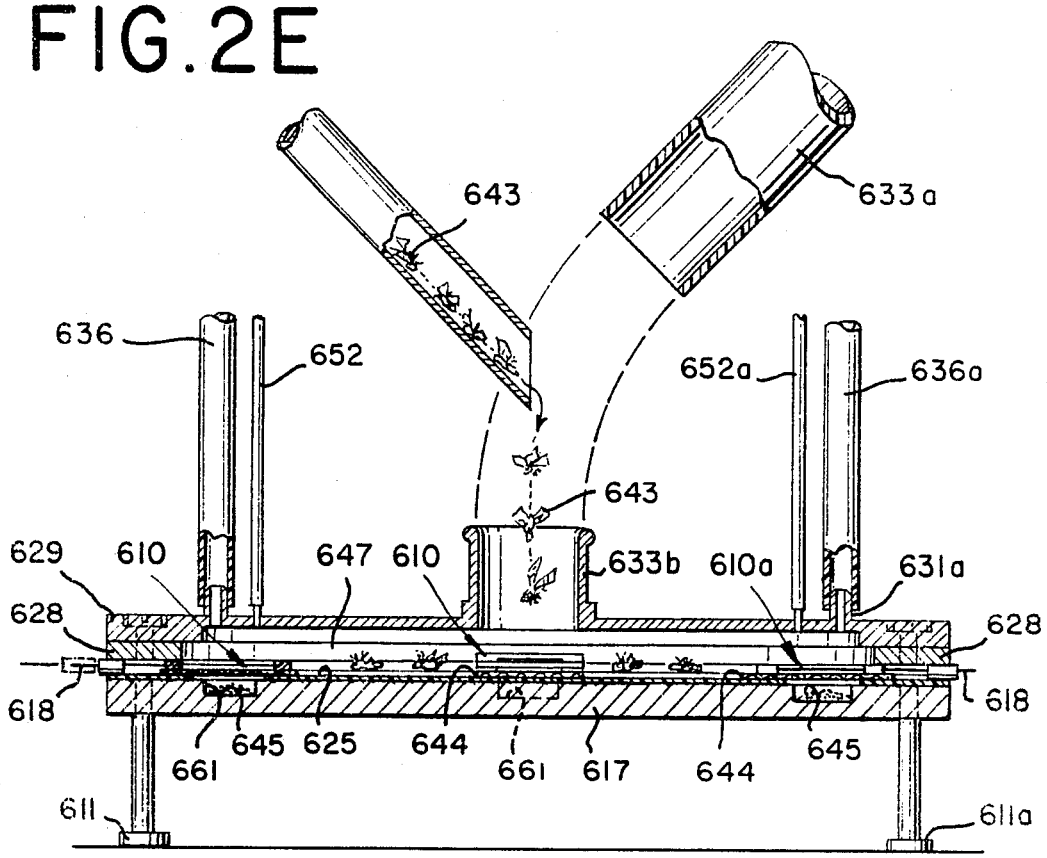
FIG. 2E is a cut-away side elevation view of the base section of the operational part of the olfactometer apparatus of FIG. 2A with air hose 633a disconnected for the purpose of placing $CO_2$-anaesthitized insects onto the base of the apparatus prior to operating the apparatus for the purpose of determining insect attractancy or repellency.
Figure 2F:
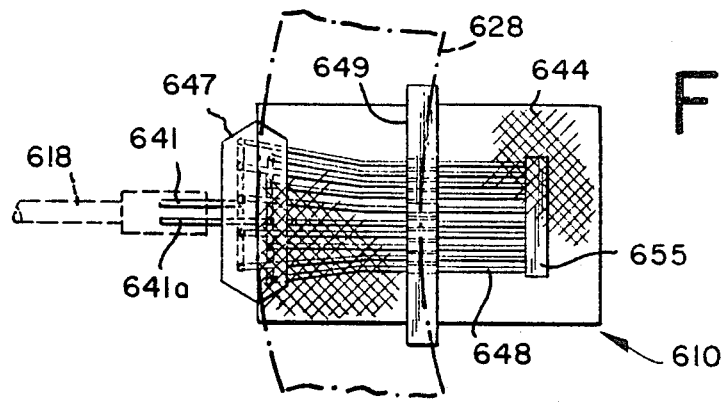
FIG. 2F is a top view of an insect feeding surface comprising spaced electrically conductive wires mounted on a silicone membrane and used in the embodiment of the olfactometer apparatus as illustrated in FIGS. 2A, 2B, 2C, 2D and 2E.
Figure 2G:
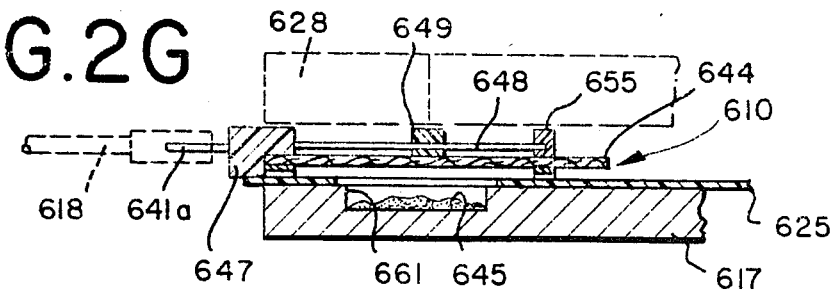
FIG. 2G is a cut-away side elevation view of the insect feeding surface comprising spaced electrically conductive wires of FIG. 2F.
Figure 2H:
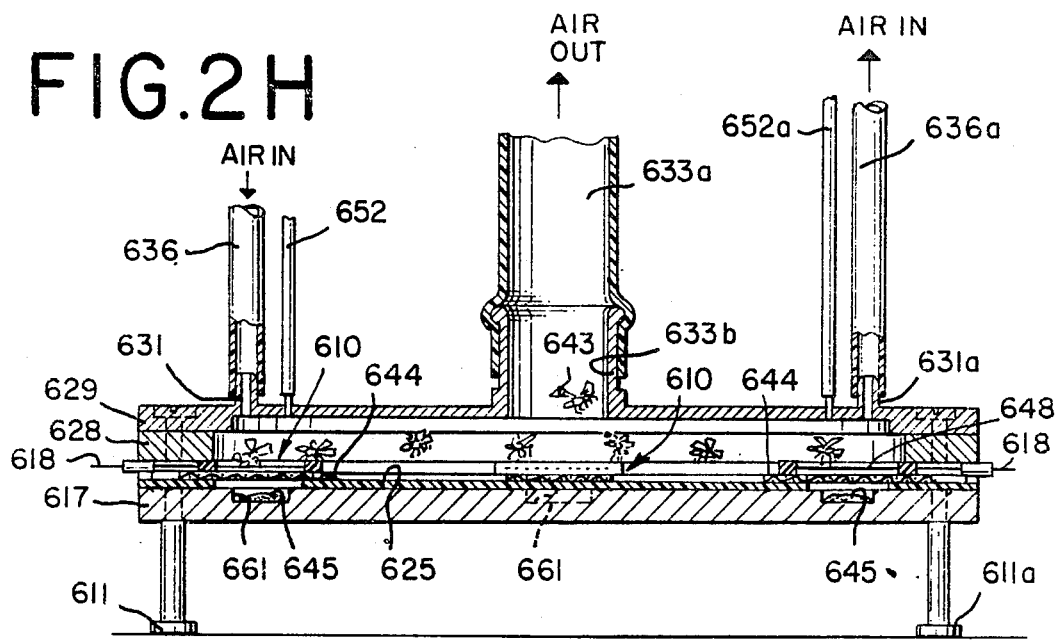
FIG. 2H is a cut-away side elevation view of the base section of the apparatus of FIG. 2D showing air hose 633a connected and the apparatus in operation with insects 643 located on the insect feeding surface comprising spaced electrically conductive wires.
Figure 2J:
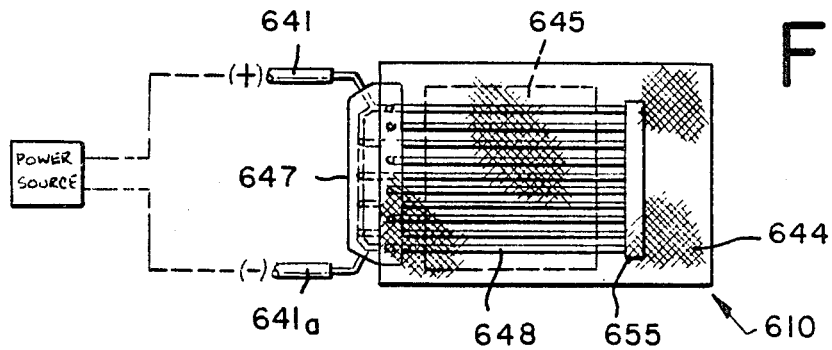
FIG. 2J is a top view of a second embodiment of the insect feeding means 610 comprising spaced electrically conductive wires.
Figure 2K:
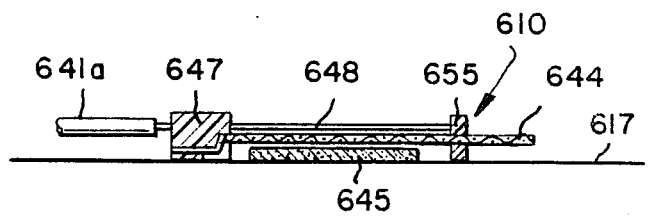
FIG. 2K is a cut-away side elevation view of the insect feeding means of FIG. 2J.

Referring to FIGS. 2E, 2F and 2G, the insect feeding surface in this second embodiment of our invention comprises a number of spaced electrically conductive wires 648 held in place by holders 647 and 655 and coated with a silicone resin for sealing purposes 649. Wires 648 are combined into positive leads 641 and negative leads 641a. The wires 648 are held in place above a membrane 644, actually a silicone membrane as described in detail in the Davis, et al paper (J. Med. Entomol. Volume 20, No. 2: 177–182) and the Butler, et al paper in ACAROLOGY VI, Volume 2 cited, supra (indicated as a "Reinforced Silicone Membrane"). Beneath this membrane 644 is the insect nutrient composition of matter or insect food 645 as shown specifically in FIG. 2G. Also holding the wires in place is holder 647 shown in detail in FIG. 2G.

Prior to operation of the olfactometer for testing the insects for attractancy to certain molecules, e.g., 1-nonen-3-ol, air hose 633a is disconnected from joint 633b in order to place anaesthitized (via $CO_2$) insects 643 onto surface 617. After the insects 643 are placed on surface 617 air hose (for the purposes of air exhaust) 633a is connected at joint 633b in an air tight manner and air is passed through lines 636, 636a et seq. and simultaneously light is radiated through light guides 652, 652a et seq., thus de-anaesthetizing the insects and causing them to be either attracted or not to the proximity or surface of wires 648. Even if the insects are attracted to the proximity of wires 648 an electric field is generated thereby giving rise to an electric current in wires 618 (due to the close spacing of the wires 648) thereby causing a "readout" from the computer system.

Figure 3:
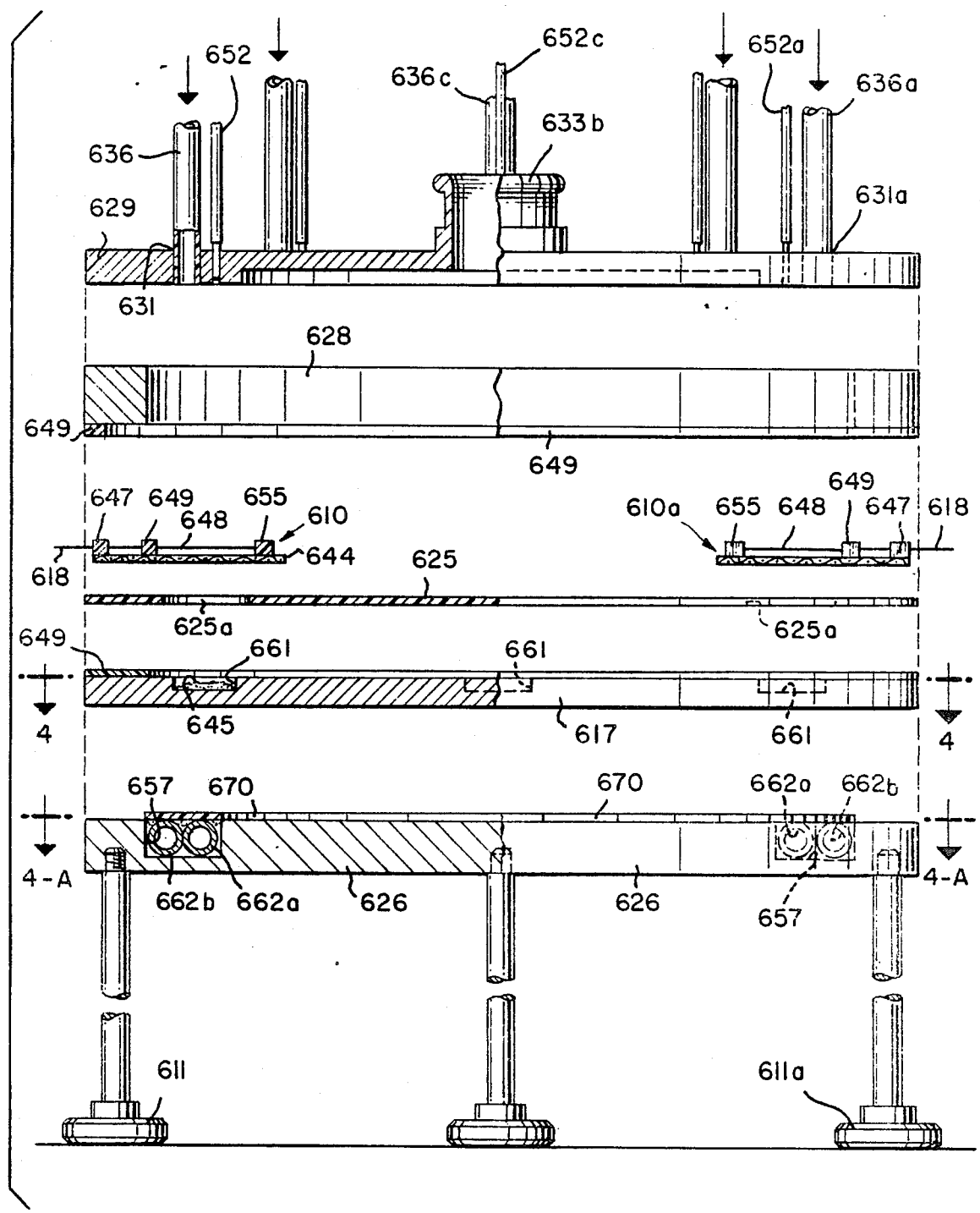
FIG. 3 is a schematic diagram (blown up for illustration purposes) of a cut-away side elevation view of a section of the olfactometer apparatus of the embodiment of FIG. 2D useful in ascertaining, inter alia, the efficacy of the 1-nonen-3-ol as a repellent for house flies (*Musca domestica*) without indicating the utilization of the computer-assisted efficacy measuring apparatus; but only indicating a section of the operational portion of the olfactometer apparatus.
Figure 4:
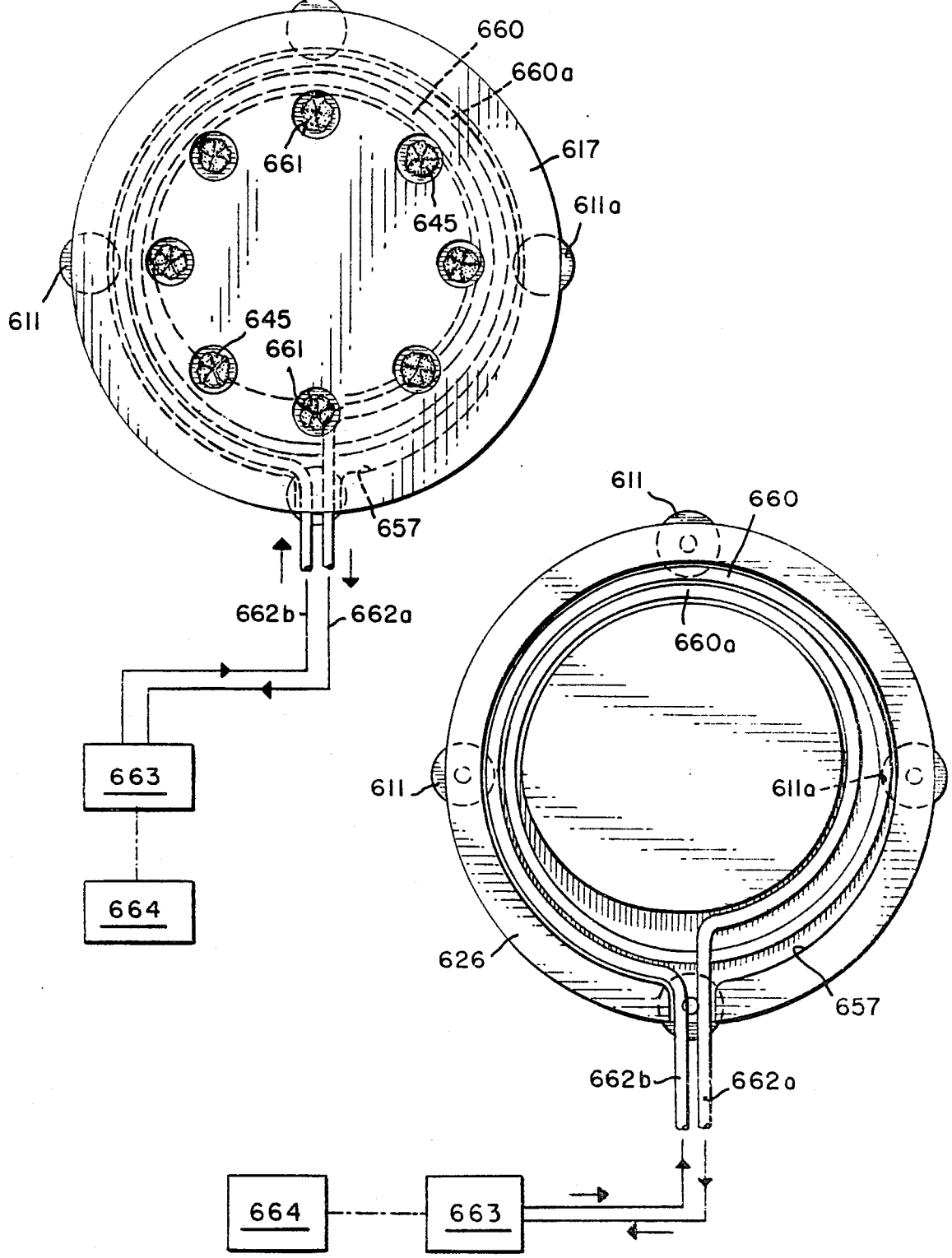
FIG. 4 is the top view of the lower section of an embodiment of the olfactometer apparatus of FIG. 2D, looking down at facing plate 617, indicating in schematic block flow diagram form the utilization of heat transfer and forced fluid flow apparatus in schematic block flow diagram form.

FIG. 3 is a cut-away side elevation schematic view of a detailed section of the olfactometer of our invention and is in fact a third embodiment of the olfactometer of our invention indicating the presence of heating coils 650 and 662 in base plate 626. Air is fed in through lines 636 while light is radiated through light guide 652 both held in place on plate 629. Plate 629 is spaced at a reasonable distance (e.g., 1.0") using spacer ring 628 which is sealed in place via silicone seals 649. The silicone seals 649 are, for example, holding sensor 610 in place. Sensor 610 is located on silicone membrane 644 and is located on a thin polymeric continuous film, e.g., SARAN®WRAP 625 which is located on face plate 617. The SARAN®WRAP contains a plurality of radially spaced openings 625 directly corresponding to feed wells 661. Thus, face place 617 contains a well for liquid feeds 661 which is situated directly beneath the location of sensors 610. Face plate 617 is preferably constructed of aluminum. Face plate 617 is in direct face-to-face contact with base plate 626 which contains cavity 657 for heating coils 650 and 662. Base plate 626 is located on a stand which is situated on dampers 611. The top view of the olfactometer looking directly down on face plate 617 is set forth in FIG. 4. The reference numeral 617 refers to the face plate per se. Wells for liquid feeds 661 are shown on face plate 617. Hidden lines 660 and 660a are representations of the heating coils through which heat transfer fluid is supplied through lines 650 and 662 (with heated water) using pump 663 the heat for which is controlled using controller 664. Coils 650 and 662a are preferably covered at cavity 657 with a heat transfer paste 670.

FIG. 4A is also a top view of the olfactometer with the face plate removed looking directly down on the base plate 626.

Figure 5:
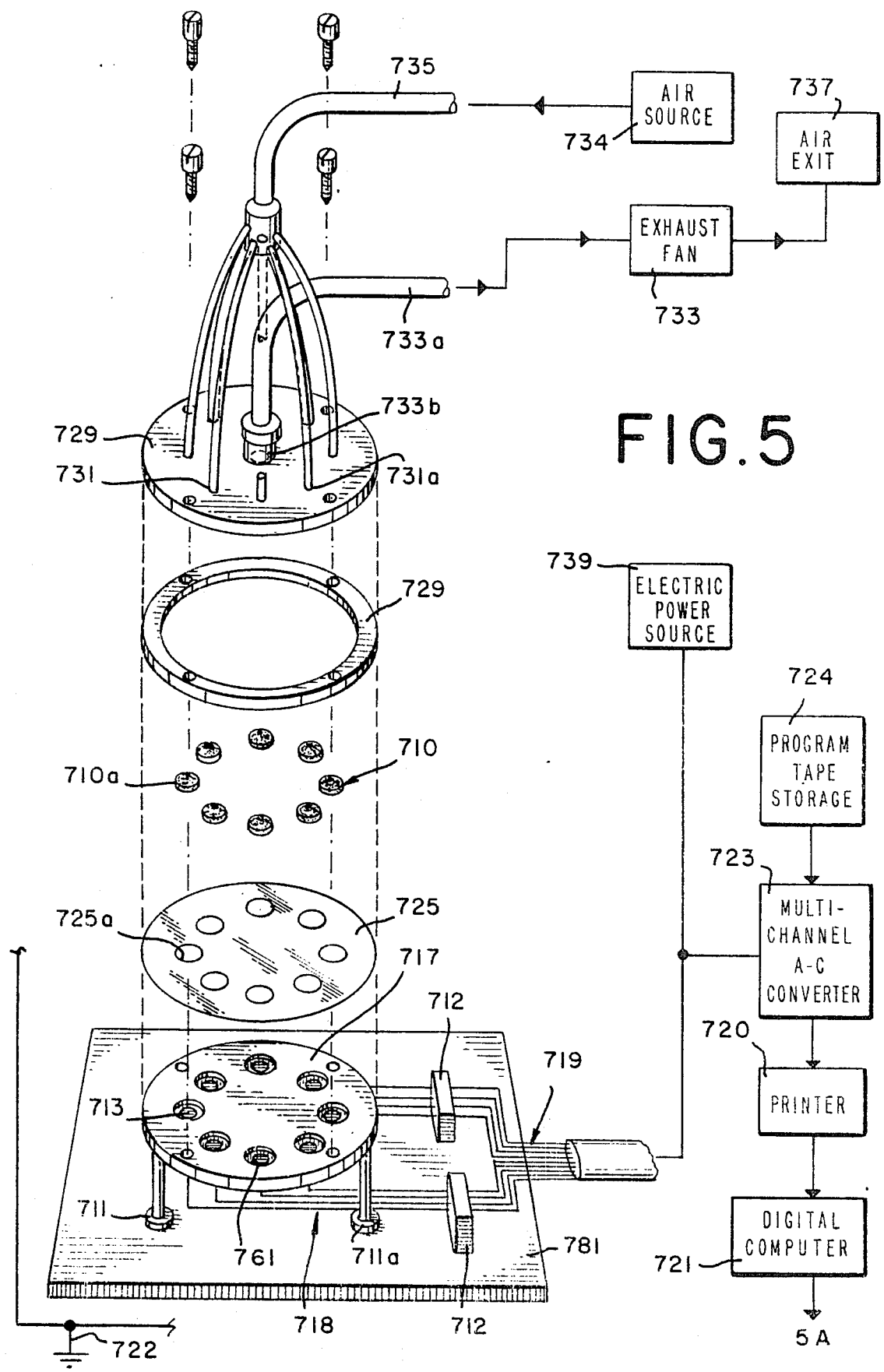
FIG. 5 is a schematic diagram (blown up for illustration purposes) of another embodiment of the olfactometer apparatus of our invention useful in ascertaining the efficacy, inter alia, of 1-nonen-3-ol as a repellent for house flies (*Musca domestica*) indicating in schematic block flow diagram form the utilization of computer-assisted efficacy measuring apparatus.

FIG. 5 is a exploded view of a fourth embodiment of the olfactometer apparatus used in testing the efficacy of, interalia, 1-nonen-3-ol as a house fly (*Musca domestica*) attracting material. Air source 734 feeds air through line 735 through air distributors 736, 736a et seq. onto base plate 717 containing insect landing sites 710, 710a et seq. The base plate 717 is separated from the spacer plate 729 for the air lines 736, 736a et seq. whereby the air lines 736, 736a et seq. are held in place at positions 731 and 731a. Air exits through line 733a using exhaust fan 733 at air exit 737. The olfactometer is assisted with computer apparatus shown in schematic form and block flow diagram form using reference numeral 720, 721, 723, 724 and 739. Dampers 711a, 711b et seq. hold base plate 717 in place horizontally. When an insect lands on sensor landing site 710, 710a et seq. the landing is recorded electrically through a sensor shown in magnified form in FIG. 5A. The sensor landing site includes a transducer 713 and causes an electrical impulse to proceed through wire 718 and then through wire 719 to a multi-channel A-D converter 723 (using electric power source 739) which is associated with program tape storage 724, printer 720 and digital computer which is associated with modem and main frame 721. Reference numeral 722 shows a "Faraday" cage completing the olfactometer circuit. The electric impulse thus effects a recording of the data as set forth in Table I, supra.

FIG. 5A is a partial cross section of FIG. 5 showing one specific landing site 710a on which the insect lands if attracted by 1-nonen-3ol or does not land if repelled by the 1-nonen-3-ol which is also located at specific landing sites. At other landing sites nothing is located (and these are the "control" landing sites). The olfactometer includes a base 781 on which the damper 711a, 711b et seq. are located, namely base 781. Base plate 717 is preferably covered with a film such as SARAN® WRAP 725 so that any insects that are attracted to the landing sites are not distracted to any other areas on base plate 717.

Figure 6:
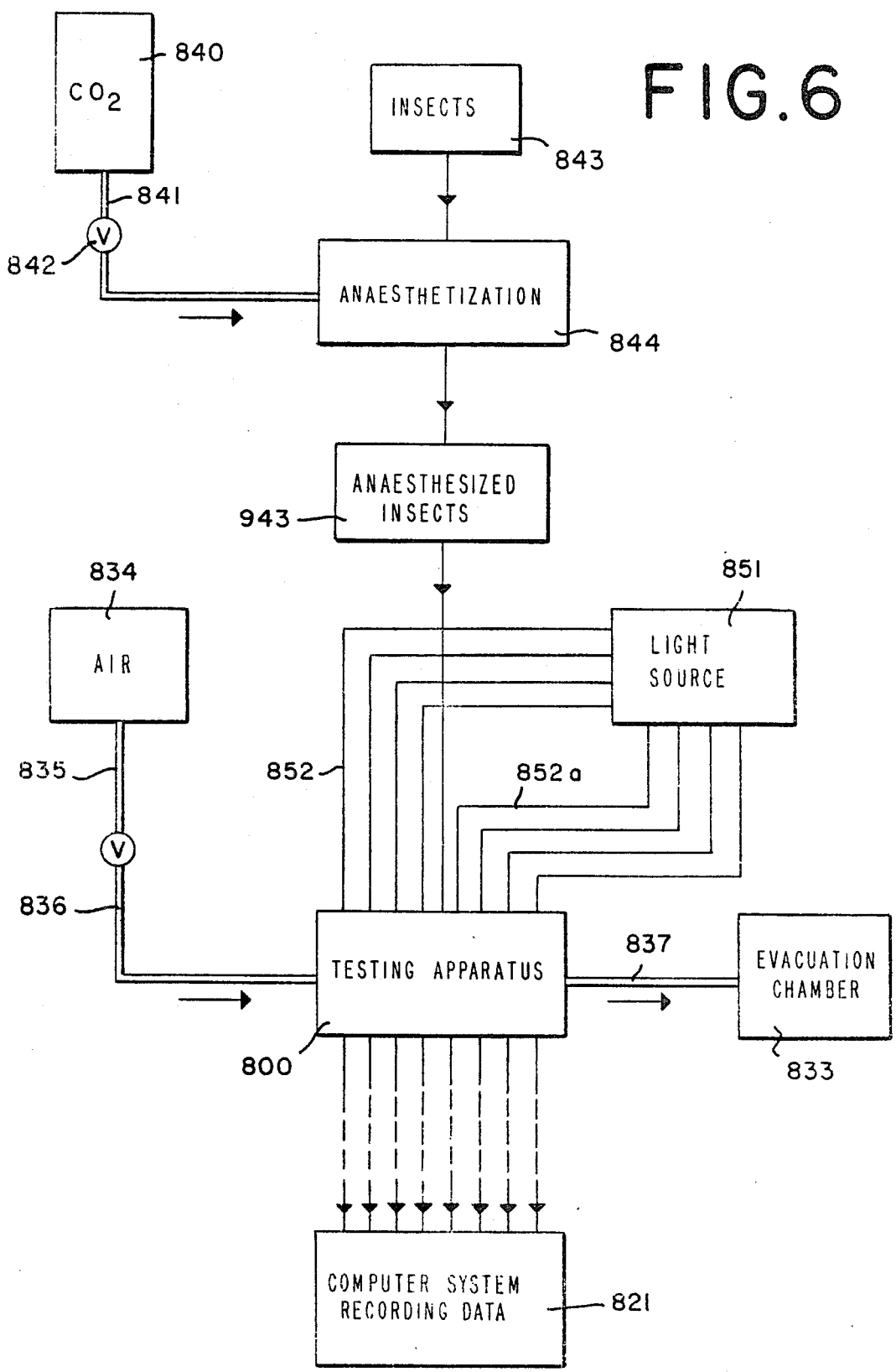
FIG. 6 is a schematic block flow diagram setting forth the process of our invention for testing repellency and attractancy of molecules using such apparatus as is set forth in FIGS. 1, 2A, 2D and 5.

FIG. 6 is a block flow schematic diagram indicating the process of our invention. Insects 843 are anaesthetized at 844 using anaesthetizing gas 840 past through lines 841 and valve 842. The anaesthetized insects at 943 are placed in testing apparatus 800. The testing apparatus is closed except for introduction of air and, optionally light. Air at 834 is past through line 835 past valve 836 into the testing apparatus with, optionally light from source 851. The air leaves the testing apparatus through line 837 into evacuation chamber 833. When the air is past through the testing apparatus with, optionally, light, the insects are de-anaesthetized and are attracted to attraction sites, if, indeed, the molecules at the attraction sites attract the insects. When the insects are near or on the attraction sites, the attraction sites cause an impulse into a computer system which records data at 821.

Figure 7:
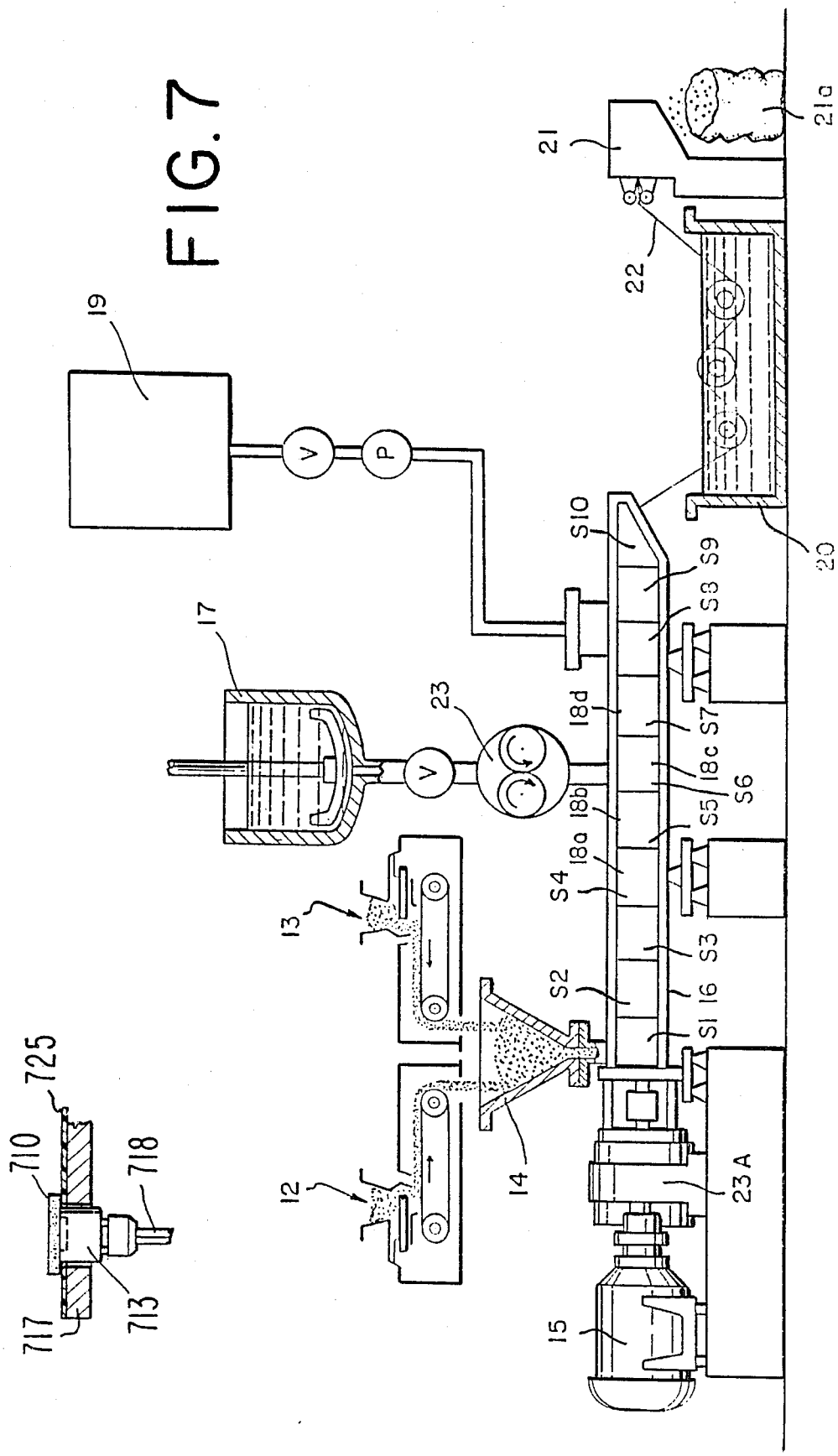
FIG. 7 is a cut-away side elevation schematic diagram of a screw extruder operating during the compounding of a polymer, (e.g., polyethylene) with the 1-nonen-3-ol repellent while simultaneously adding foaming agent into the hollow portion of the barrel of the extruder and incorporates the pelletizing apparatus used in pelletizing the extruded foamed tow produced as a result of the extrusion operation.
Figure 8:
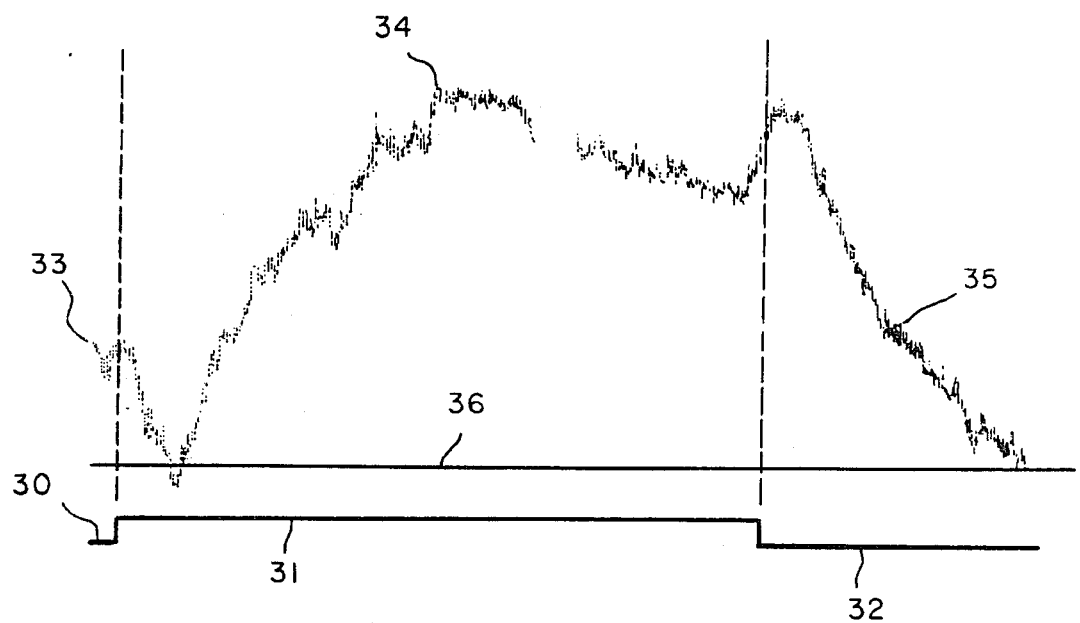
FIG. 8 is a graph of neural signal vs. time recorded from the antennal nerve of the house fly (*Musca domestica* L.), (Diptera:Muscidae)) using the attractant called "extract of used fly rearing media" (mixture of manures, alfalfa and baking soda) as the stimulus.

FIG. 7 is a schematic cut-away elevation diagram of the extrusion and pelletizing apparatus useful in carrying out the process of our invention during the operation of said apparatus. Motor 15 drives the extruder screws located at 23A in barrel 16, the extruder being operated at temperatures in the range of about 150° up to about 250° C. At the beginning of the barrel resin at source 12 together with processing aids at location 13 is added via addition funnel 14 into the extruder. Simultaneously (when the operation reaches "steady state"), 1-nonen-3-ol is added to the extruder at one two or more of barrel S-3, S-4, S-5, S-6, S-7 and S-8 of the extruder (which may be a twin screw or single screw extruder) at locations 18a, 18b, 18c and 18d, for example, by means of gear pump 23 from source 17. From source 19 into barrel segments S-5, S-6, S-7, S-8, S-9 and S-10, optionally, the gaseous or liquid blowing agents, e.g., nitrogen, carbon dioxide and the like as described, supra, are added simultaneously with the addition of the 1-nonen-3-ol. The feed rate range of resin is about 80–300 pounds per hour. The feed rate range of 1-nonen-3-ol is between 1 and 35% of the feed rate range of the resin. The blowing agent rate range (when the blowing agent is used) is such that the pressure of the gas or the pressure over the liquid being fed into the extruder is between about 50 and 200 psig. If desired, the extruded ribbon or cylinder may be passed through water bath 20 and pelletizer 21 into collection apparatus 21a. FIG. 8 sets forth the neural signal recorded from the antennal nerve of the *Musca domestica* L. (Diptera:Muscidae) using the attractant called "Extract of used fly rearing media " (mixtures of manures, alfalfa and baking soda) as the stimulus. Passage of the attract to the *Musca domestica* L. (Diptera:Muscidae) is indicated at reference numeral 31 whereas reference numerals 30 and 32 indicate no passage of the treating material to be tested. When passage of the test material takes place the neural signal is indicated at reference numeral 34 When there is no passage of the test material the neural signal is indicated at reference numeral 33 and at reference numeral 35. Reference numeral 36 is the base line for neural signal recorded from the antennal lobe using the attractant called "Extract of used fly rearing media".

Figure 9:
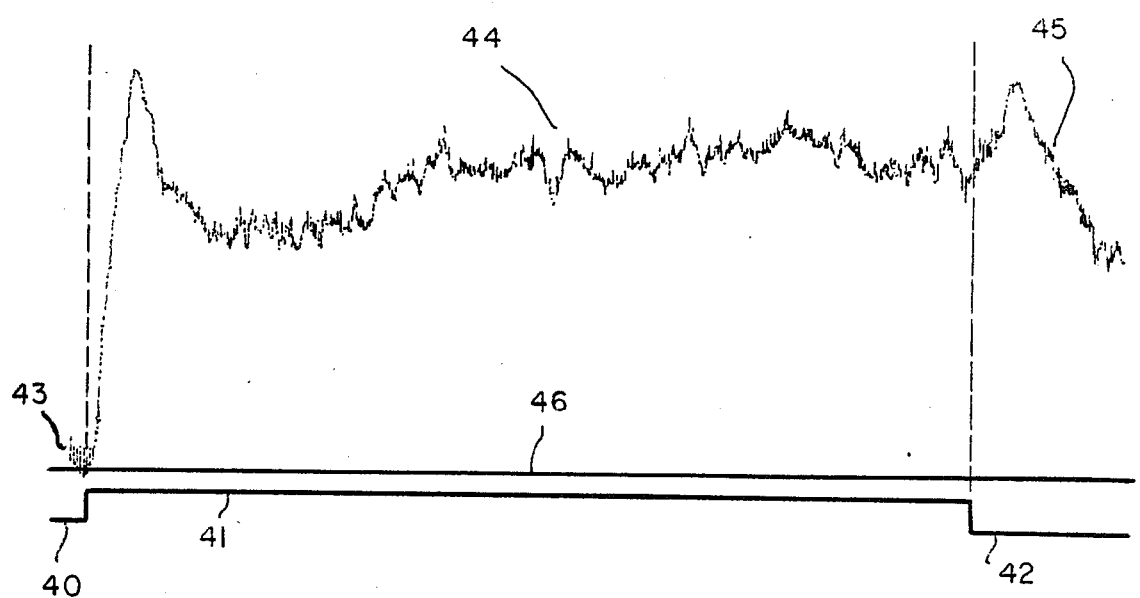
FIG. 9 is a graph of the neural signal vs. time recorded from the antennal nerve of the *Musca domestica* L. (Diptera:Muscidae) (house fly) using the repellent, 1-nonen-3-ol as the stimulus.

FIG. 9 sets forth the neural signal recorded from the antennal nerve of the *Musca domestica* L. (Diptera:Muscidae) using the repellent 1-nonen-3-ol. The neural signal in FIG. 9 is set forth and is shown using reference numerals 43, 44 and 45 and the passage or treatment period is shown using reference numerals 40, 41 and 42. Reference numerals 40 and 42 show no passage of test material, e.g., 1-nonen-3-ol. The neural signal recorded when no passage of test material takes place is set forth at reference numerals 43 and 45 (respectively for periods 40 and 42). The neural signal recorded when test material is used to treat the *Musca domestica* L. (Diptera:Muscidae) is set forth at reference numeral 44. The base line for the neural signal recorded from the antennal nerve using 1-nonen-3-ol is indicated by reference numeral 46. The change from the base line during treatment (41) is indicative of the fact that the 1-nonen-3-ol is a strong repellent for *Musca domestica* L. (Diptera:Muscidae).

Figure 10:
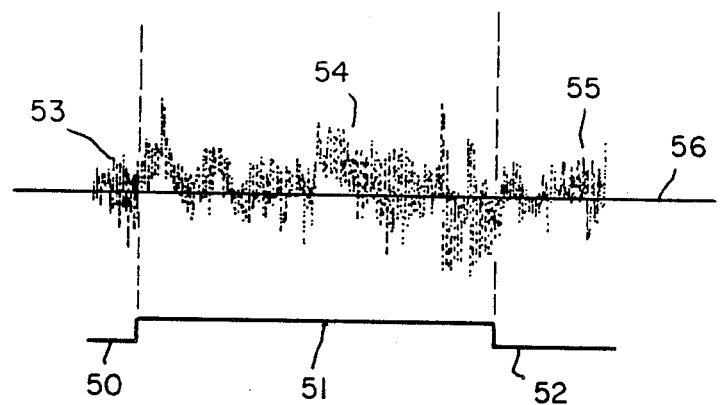
FIG. 10 is a graph of neural signal vs. time recorded from the funiculus of the house fly (*Musca domestica* L. (Diptera:Muscidae)) using the attractant called "extract of used fly rearing media" (mixture of manures, alfalfa and baking soda) as the stimulus.

FIG. 10 sets forth the neural signal recorded from the funuculus of *Musca domestica* L. (Diptera:Muscidae) using the attractant "Extract of used fly rearing media" as described, supra. Passage of the attractant to the *Musca domestica* L. (Diptera:Muscidae) is indicated at reference numeral 51 whereas reference numerals 50 and 52 indicate no passage of the treating material to be tested. When passage of the test material takes place the neural signal is indicated at reference numeral 54 whereas reference numerals 53 and 55 indicate no passage of the treating material to be tested. When passage of the test material takes place the neural signal is indicated at reference numeral 54. When there is no passage of the test material the neural signal is indicated at reference numeral 53 and at reference numeral 55. reference numeral 56 is the base line for the neural signal recorded from the funuculus using the attractant "Extract of used fly rearing media". The lack of any change from the base line during treatment (51) is indicative of the fact that the "Extract of used fly rearing media" is a strong attractant for *Musca domestica* L. (Diptera:Muscidae).

Figure 11:
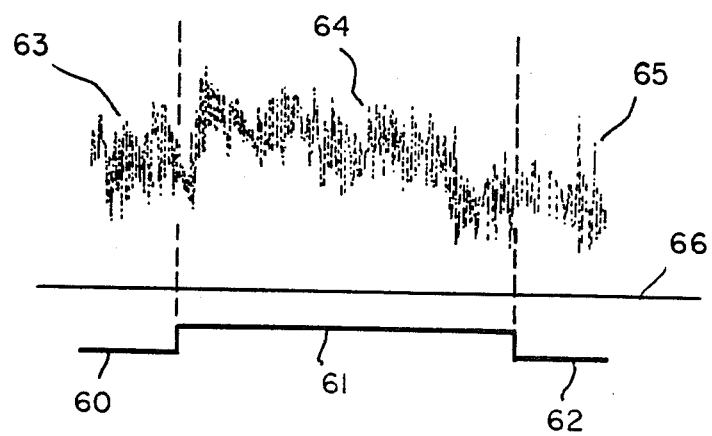
FIG. 11 is a graph of neural signal vs. time recorded from the funiculus of the *Musca domestica* L. (Diptera:Muscidae) (house fly) using the repellent 1-nonen-3-ol as the stimulus.

FIG. 11 sets forth the neural signal recorded from the funuculus of the *Musca domestica* L. (Diptera:Muscidae) using 1-nonen-3-ol. The neural signal in FIG. 11 is set forth and is shown using reference numerals 63, 64 and 65 and the passage or treatment period is shown using reference numerals 60, 61 and 62. Reference numerals 60 and 62 show no passage of the test material, the 1-nonen-3-ol. The neural signal recorded when no passage of test material takes place is set forth at reference numerals 63 and 65 (respectively, for period 60 and 62). The neural signal recorded when test material is used to treat the *Musca domestica* L. (Diptera:Muscidae) is set forth at reference numeral 64. The base line for the neural signal recorded from the funuculus using 1-nonen-3-ol is indicated by reference numeral 66. The change from the base line during treatment (61) is indicative of the fact that the 1-nonen-3-ol is a strong repellent for *Musca domestica* L. (Diptera:Muscidae).

Figure 12:
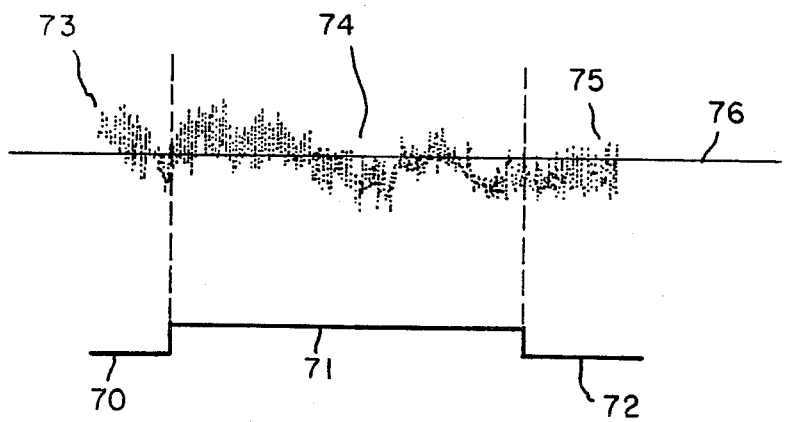
FIG. 12 is a graph of neural signal vs. time recorded from the antennal base of the house fly (*Musca domestica* L. (Diptera:Muscidae)) using the attract called "extract of used fly rearing media" (mixture of manures, alfalfa and baking soda) as the stimulus.

Referring to FIG. 12, FIG. 12 sets forth the neural signal recorded from the antennal base of *Musca domestica* L. (Diptera:Muscidae) using the attractant called "Extract of used fly rearing media" as described, supra. Passage of the attractant to the *Musca domestica* L. (Diptera:Muscidae) is indicated at reference numeral 71 whereas reference numerals 70 and 72 indicate no passage of the treating material to be tested. When passage of the test material takes place the neural signal is indicated at reference numeral 74. When there is no passage of the test material the neural signal is indicated at reference numeral 73 and at reference numeral 75. Reference numeral 76 is the base line for the neural signal recorded from the antennal lobe using the attractant "Extract of used fly rearing media". The lack of any change from the base line during treatment 71 is indicative of the fact that the "Extract of used fly rearing media" is a strong attractant for *Musca domestica* L. (Diptera:Muscidae).

Figure 13:
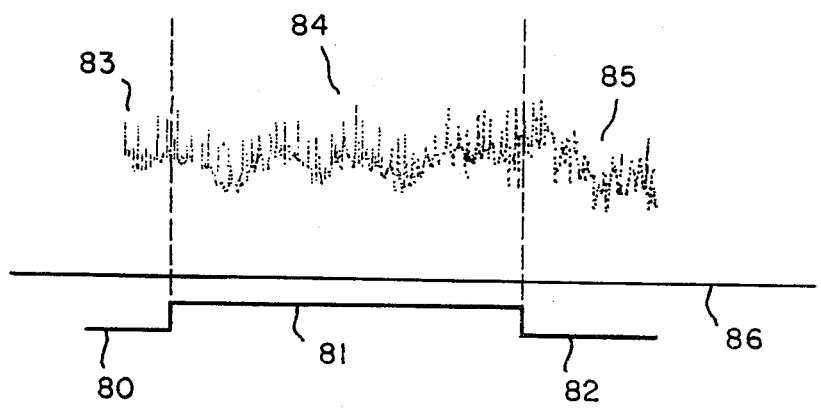
FIG. 13 is a graph of neural signal vs. time recorded from the antennal base of the *Musca domestica* L. (Diptera:Muscidae) (house fly) using the repellent 1-nonen-3-ol as the stimulus.

FIG. 13 sets forth the neural signal recorded from the antennal base of the (*Musca domestica* L. (Diptera:Muscidae)) using 1-nonen-3-ol. The neural signal in FIG. 13 is set forth and is shown using reference numerals 83, 84 and 85 and the passage treatment period is shown using reference numerals 80, 81 and 82. Reference numerals 80 and 82 show no passage of test material, e.g., 1-nonen-3-ol. The neural signal recorded when no passage of test material takes place is set forth at reference numerals 83 and 85 (respectively, for periods 80 and 82). The neural signal recorded when test material is used to treat the *Musca domestica* L. (Diptera:Muscidae) is set forth at reference numeral 84. The base line for the neural signal recorded from the antennal base using 1-nonen-3-ol is indicated by reference numeral 86. The change from the base line during treatment (81) is indicative of the fact that the 1-nonen-3-ol is a strong attractant for *Musca domestica* L. (Diptera:Muscidae).

Figure 14:
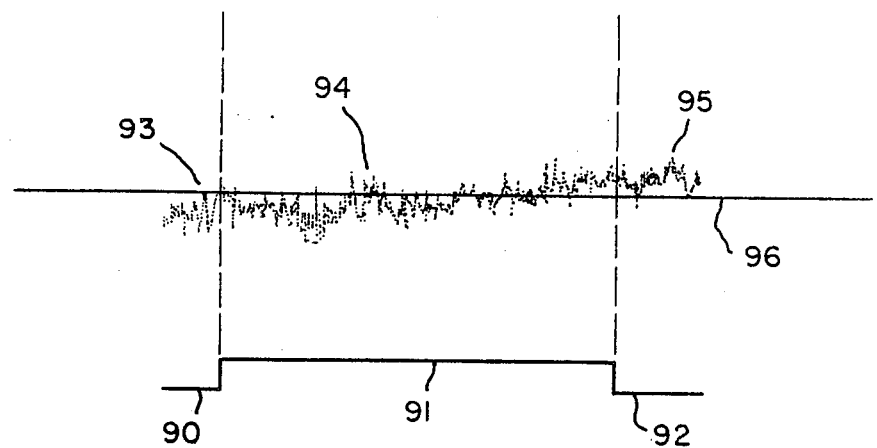
FIG. 14 is a graph of neural signal vs. time recorded from the antennal lobe of the house fly (*Musca domestica* L. (Diptera:Muscidae)) using the attractant called "extract of used fly rearing media" (mixture of manures, alfalfa and baking soda) as the stimulus.

Referring to FIG. 14, FIG. 14 sets forth the neural signal recorded from the antennal lobe of *Musca domestica* L. (Diptera:Muscidae) using the attractant called "Extract of used fly rearing media" as described, supra. Passage of the attractant to the *Musca domestica* L. (Diptera:Muscidae) is indicated at reference numeral 91 whereas reference numerals 90 and 92 indicate no passage of the treating material to be tested. When passage of the test material takes place the neural signal is indicated at reference numeral 94. When there is no passage of the test material the neural signal is indicated at reference numerals 93 and 95. Reference numeral 96 is the base line for the neural signal recorded from the antennal lobe using the attractant called "Extract of used fly rearing media". The lack of any change from the base line during treatment (91) is indicative of the fact that the "Extract of used fly rearing media" is a strong attractant for *Musca domestica* L. (Diptera:Muscidae).

Figure 15:
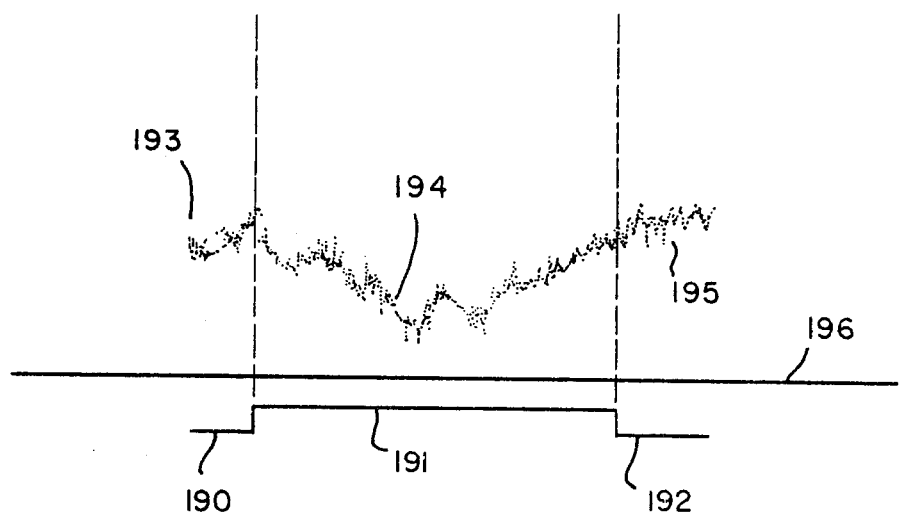
FIG. 15 is a graph of neural signal vs. time recorded from the antennal lobe of the *Musca domestica* L. (Diptera:Muscidae) (house fly) using the repellent 1-nonen-3-ol as the stimulus.
Figure 16:
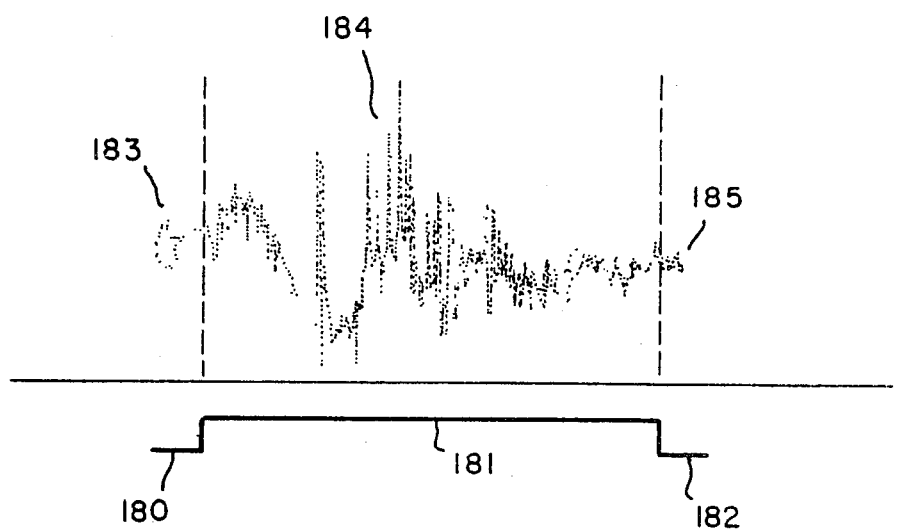
FIG. 16 is another graph of neural signal vs. time recorded from the antennal lobe of the *Musca domestica* L. (Diptera:Muscidae) (house fly) using the repellent 1-nonen-3-ol as the stimulus.

FIGS. 15 and 16 set forth the neural signals recorded from the antennal lobes of the *Musca domestica* L. (Diptera:Muscidae) using 1-nonen-3-ol. The neural signal in FIG. 15 is set forth and is shown using reference numerals 193, 194 and 195 and the passage or treatment period is shown using reference numerals 190, 191 and 192. Reference numerals 190 and 192 show no passage of test material, e.g., 1-nonen-3-ol. The neural signal recorded when no passage of test material takes place is set forth at reference numeral 193 and 195 (respectively, for periods 190 and 192). The neural signal recorded when test material is used to treat the *Musca domestica* L. (Diptera:Muscidae) is set forth at reference numeral 194. The base line for the neural signal recorded from the antennal lobe using 1-nonen-3-ol is indicated by reference numeral 196. The change from the base line during treatment (191) is indicative of the fact that the 1-nonen-3-ol is a strong repellent for *Musca domestica* L. (Diptera:Muscidae).

The neural signal in FIG. 16 is set forth and is shown using reference numerals 183, 184 and 185 and the passage or treatment period is shown using reference numerals 180, 181 and 182. Reference numerals 180 and 182 show no passage of the test material, e.g., 1-nonen-3-ol. The neural signal recorded when no passage of test material takes place is set forth at reference numerals 183 and 185 (respectively, for periods 180 and 182). The neural signal recorded when test material is used to treat the *Musca domestica* L. (Diptera:Muscidae) is set forth at reference numeral 184. The base line for neural signal recorded from the antennal lobe using 1-nonen-3-ol is indicated by reference numeral 186. The change from the base line during treatment (181) is indicative of the fact that the 1-nonen-3-ol is a strong attractant for *Musca domestica* L. (Diptera:Muscidae).

Figure 17:
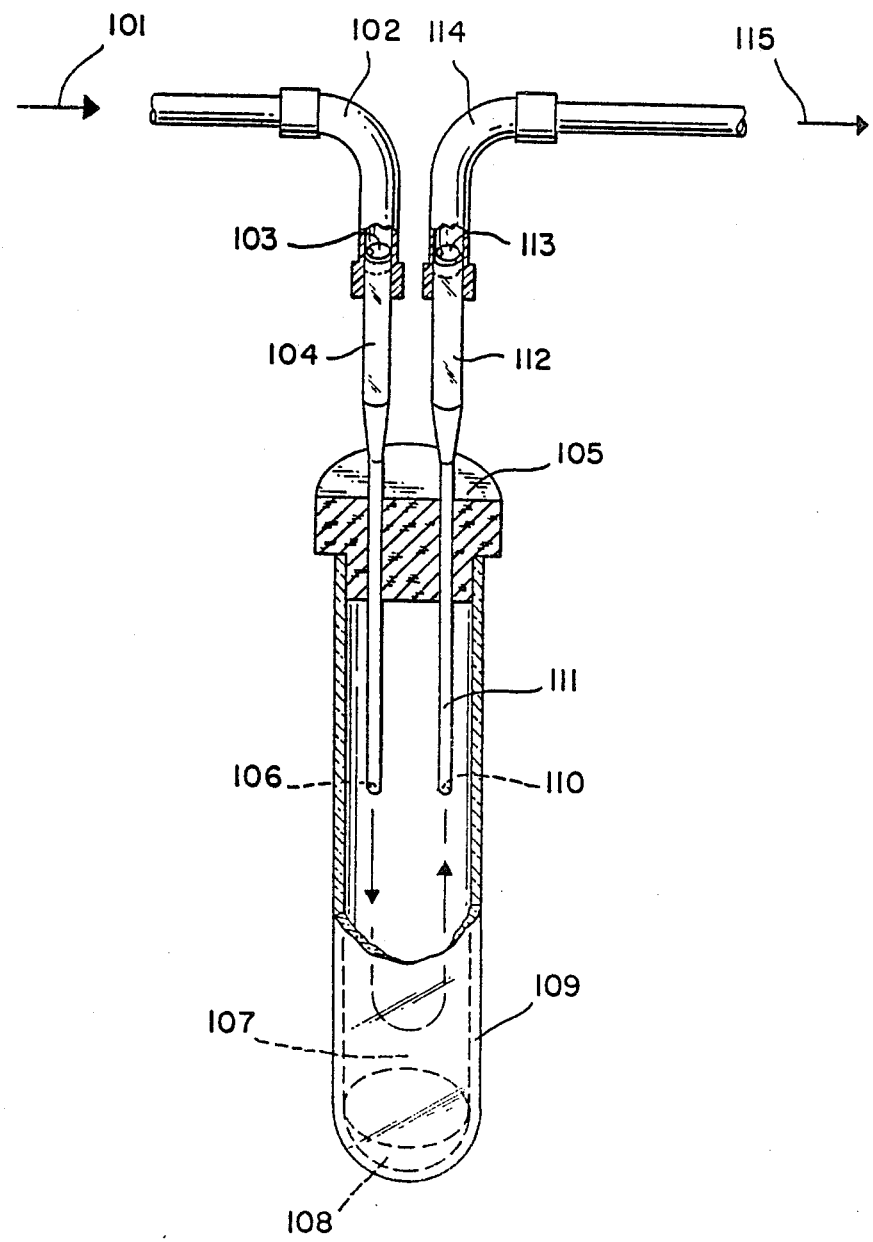
FIG. 17 is a perspective view of the odor delivery system used to supply odor to the house fly (*Musca domestica* L. (Diptera Muscidae)) when collecting data from the electrophysiological study of the neural correlates of attraction and repulsion in the house fly (*Musca domestica* L. (Diptera:Muscidae)).

FIG. 17 is a diagram in perspective, of an odor delivery system used to supply such materials as 1-nonen-3-ol to the fly. When applying the attractant or repellent to be tested to the fly, air from a pressurized air tank is fed through line 101 at location 102 through a valve through pipette 103/104 through orifice 106 into tube 109 containing the media to be tested, e.g., 1-nonen-3-ol, indicated by reference numeral 108. The headspace 107 over the media 108 will thus include molecules of air as well as the material to be tested, e.g., 1-nonen-3-ol. The resulting mixture of air and attractant or repellent is then passed through orifice 110 through tube 111-112-113 through tube 115 (at location 114) to the location where the fly (*Musca domestica* L. (Diptera:Muscidae)) reactions are being measured. Tubes 104 and 112 are held in place by holder 105.

The house flies used for this study were supplied from a laboratory colony at the medical and veterinary entomology laboratory at the University of Florida. A female, 3–7 day old fly was restrained on a standard microscope slide using the following technique. The fly's wings were clipped off near the base in order to facilitate handling. The fly was then glued to the microscope slide, dorsal side down, using Super glue. Ski wax was melted around the head capsule to immobilize the head during electrode penetration. The slide was then placed under a dissecting microscope to enable a more accurate placement of the electrode.

Microcapillary electrodes (tip O.D. 1-5 mm) were filled with an ionic fluorescent solution which served the dual purpose of a conducting solution as well as marking the recording site. The ionic solution contained Lucifer yellow CH, a superfluorescent lithium salt of 3,6-disulphonate 4-aminonaphthalimide (Stewart, W. W. 1978 "Functional connections between cells as revealed by dye-coupling with a highly fluorescent naphthalimide tracer" Cell 14: 741-759), which is taken up by depolarizing neurons via induced endocytosis (Wilcox and Franceschini, N. 1984 "Illumination induces dye incorporation in photoreceptor cells" Science (Washington, D.C.) 225: 851-854.).

The active electrode was positioned in the selected spot using Nashike micromanipulators with remote hydraulic drive. Areas for electrophysiological study were located using (Strausfeld, N.J. 1978 "Atlas of an insect brain", Springer-Verlag: Berlin) (1976) detailed anatomical study of the house fly brain, which includes a three-dimensional coordinate system. Subsequent gross dissections showed that with much practice, individual lobes on the brain could be penetrated with repeatable accuracy.

The indifferent electrode was placed either in the head capsule or thorax. The preferred position was the thorax as this places the electrode out of the way. However, care must be taken not to place the indifferent electrode in the ventral nerve cord as this results in extraneous nerve signals.

In placing the active elecrode, it was necessary to prick the cuticle with a minuten pin in order to prevent deformation of the head capsule as the electrode penetrated. This method minimized damage to the underlying neural tissue.

Nerve signals were preamplified with custom neutral amplifirs at 100X and then displayed on a Nicolet 3091 oscilloscope. The same signal was simultaneously sent to a Dianachart smart recorder/data logger to obtain a hard copy of the neural signal. The olfactory stimulus was initially supplied using the technique developed by (Kauer, J. S.; Shepherd, G. M. 1975 "Olfactory stimulation and monitored step pulses of odor", Brain Res. 85: 108–113) and (Getchel, T. V.; Shepherd, G. M. 1978 "Responses of olfactory receptor cells to step pulses of odor at different concentrations in the salamander", J. Physiol. 282: 521–540) which uses three concentric pipettes, one to apply the odor and the other two to exhaust the odor. However, this system proved to be too bulky for house flies due to their small size, as it was not possible to form three concentric pipettes which were small enough not to be bulky, but not so small as to restrict air flow.

Consequently, a system was developed which used pressurized air to deliver the odor and an exhaust system was built around the entire set up. The delivery system was a test tube containing 2 ml of odor extract, stoppered, and with two disposable pipettes through the rubber stopper through the rubber stopper (as is shown in FIG. 10). One pipette 104 was attached to a pressurized air tank and the other pipette 112 was attached to a tygon tube terminating in a capillary tube which could be positioned directly in front of the fly's antennae.

Odor delivery (e.g., 1-nonen-3-ol) was controlled with a valve so that abrupt onset of the stimulus was possible. Each stimulus was approximately 4–5 seconds in duration. A minimum of 15 minutes was used between odor stimulus to allow the previous odor to be completely exhausted from the area.

When using the embodiment of our invention as set forth in FIGS. 3, 4 and 4A, the heating element is set at 36° C. and is run at 32°–36° C.

When using any of the embodiments of our invention, the air flow rate past the sensors, (e.g., sensor 241 in FIG. 3) is preferably 275 feet per minute at a temperature, preferably of 28° C. or 83° F.

When using heated apparatus as set forth in FIGS. 3, 4 and 5, it is preferable that the heating coils 260 and 260a have inside diameters of approximately 0.75 inches.

The embodiment of our invention set forth in detail in FIG. 5 (with no light being supplied to landing surfaces 710, 710a et seq.) is useful for determining attractancy and repellency of ticks because ticks feed in the dark and are attracted to a warm body. Accordingly, the use of the embodiment of FIG. 5 taken further together with the apparatus of FIGS. 3, 4 and 4a is preferred when testing ticks.

The apparatus of FIGS. 1 and 2A is preferred when testing for attractancy of flies and mosquitos. House flies (*Musca domestic* L.)(Diptera:Muscidae)) require light and no heat for a normal life. Accordingly, the apparatus of FIGS. 1 and 2A without the use of the special heating equipment of FIGS. 3, 4 and 4A is preferred when testing *Musca domestica* (Diptera:Muscidae).

Mosquitos require low light and heat when feeding. Accordingly, in testing mosquitos for attractancy and repellency the equipment of FIGS. 1 and 2A is supplemented by the special heating equipment of FIGS. 3, 4 and 4A.

EXAMPLE I

PARAFFIN WAX CANDLE BODY

The following composition is prepared:

| INGREDIENT | PARTS BY WEIGHT |
|---|---|
| Paraffin wax | 95.0 |
| 1-Nonen-3-ol | 5.0 |

The paraffin wax is intimately admixed at 150° C. and 10 atmospheres pressure with the mixture of methyl heptenone coumarin and indole in an autoclave with intensive shaking. The autoclave pressure is maintained with a nitrogen atmosphere. At the end of the period of 1 hour the autoclave is depressurized, the autoclave is opened and the resulting mixture is poured into cylindrical candle molds containing wicks.

The resulting candles on use evolve an aesthetically pleasing aroma and, in addition, give rise to efficacious house fly repellency. The candles are effective in preventing house flies from entering a room in which one candle is burning for a period of 10 minutes, the said room having dimensions of 6'×15'×15' having a 3'×3' open portal adjacent to a house fly-infested region in the month of August in the temperate zone.

EXAMPLE II

A transparent candle base mixture is produced by intimately admixing the following ingredients:

| INGREDIENT | PARTS BY WEIGHT |
|---|---|
| VERSAMID ® 1635 | 34.0 |
| Barlol 12C2 | 51.0 |
| Butyl Stearate | 3.5 |
| NEVEX ® 100 | 5.0 |
| SPAN ® 60 | 1.5 |
| Isopropyl Isostearate | 4.0 |
| Isopropyl Myristate | 4.0 |

The foregoing mixture is placed in an autoclave and intimately admixed with a perfuming-insect repellent composition containing 1-nonen-3-ol at the rate of 8% by weight of the total candle base composition.

The autoclave is sealed and heated to 180° C. under 15 atmospheres pressure and maintained with vigorous shaking for a period of 5 hours. At the end of the 5 hour period the autoclave is depressurized (being under a nitrogen pressure atmosphere) and the autoclave is opened and the contents are then poured into cyclindrical candle molds four inches in height and two inches in diameter containing 0.125" wicks. The resulting candles have efficacious insect repellencies and have aesthetically pleasing aromas on use.

The candles are effective in preventing house flies from entering a room in which two candles have been burning for 15 minutes, the said room having dimensions of 6'×15'×15' and having a 3'×3' open portal adjacent a house fly-infested region in the month of August, in the temperate zone.

EXAMPLE III

The following candle base composition of matter is prepared:

| INGREDIENT | PARTS BY WEIGHT |
|---|---|
| Polyamide (VERSAMID ® 940 manufactured by the Henkel Chemical Corporation of Minneapolis, Minnesota) | 30.0 |
| Stearic acid | 5.0 |
| Methyl-12-hydroxy stearate | 5.0 |
| 10 Carbon primary alcohol (Continental Oil Company ALFOL ® 10) further (ALFOL ® is a trademark of Conoco Division of E. I. DuPont of Wilmington, Delaware) | 5.0 |
| Myristyl Myristate | 10.0 |
| Stearic hydrazide | 0.1 |
| 1-Nonen-3-ol | 4.0 |
| Light white mineral | q.s. to 100% |

All of the materials except the polyamide are mixed at room temperature. The mixture is then heated gradually with gradual addition of the polyamide and with agitation beginning with the commencement of addition of the polyamide. In the proportion required, the polyamide does not become fully soluble until the mixture reaches the temperature of about 220° F. The temperature on the order of 220° F. to 230° F. is maintained at atmospheric pressure with continued agitation until the polyamide is fully dissolved. Since higher temperatures promote solution of the polyamide this temperature range can be slightly exceeded with some advantage.

As soon as the polyamide has dissolved completely, the mixture is poured into molds following the conventional practice in the manufacture of molded candles. As the candles cool they harden. The candles are then freed from the molds and tested for insect repellency.

The candles are effective in preventing house flies from entering a room in which two candles have been burning for 15 minutes, the said room having dimensions of 6'×15'×15' and having a 3'×3' open portal adjacent a house fly-infested region in the month of August in the temperate zone.

EXAMPLE IV

A study was conducted to evaluate the efficacy of candles which are designated as "A", "B", and "C" in repelling house flies (*Musca domestica*).

Candle "A" contained 95% Paraffin Wax and 5% of the following composition:

100 parts by weight of 1-nonen-3-ol; and 700 parts by weight of a perfume composition containing the following ingredients:

| INGREDIENT | PARTS BY WEIGHT |
|---|---|
| (i) Perfume mixture of essential oils and chemicals, to wit: the methyl ester of 2,5-dihydroxy-4-6-dimethyl benzoic acid; dihydro myrcenol; oakmoss absolute; benzyl acetate; geraniol; isobornyl acetate; citronellyl acetate; para-t-butyl phenyl isovaleraldehyde; benzyl salicylate; hexyl cinnamic aldehyde; geranonitrile; patchouli oil; alpha-terpineol; tetrahydromuguol; phenyl ethyl alcohol; cedrenal; methyl ionone; cinnamyl acetate; benzyl benzoate; | 83.8 grams |
| (ii) Solvent: the methyl ester of dihydroabietic acid | 4.0 grams |

Candle "B" contained 90% Paraffin Wax and 10% citronella oil.

Candle "C" contained only Paraffin Wax.

The candles are allowed to burn for 20 minutes and the number of house flies repelled is recorded for the next 60 minutes with the following equipment and procedure:

Materials

Test Chamber

The evaluation was conducted in a 28.3 cubic meter chamber with airing ports. A screened cage measuring 15 cm×15 cm×47.5 cm was attached inside an upper airing port, and a screened repellency observation cage measuring 15 cm×15 cm×32.5 cm was attached outside the upper airing port. The two cages were held together by a Masonite plate which fit firmly in the airing port. A 4-cm hole located in the center of each Masonite plate provided an escape for the test insects. A barrier was used to close the hole.

Attractant

A caged mouse was used as an attractant and was placed inside the chamber in the larger section of the repellency cage.

Test Insect

Adult house flies (*Musca domestica*) are test insects.

Procedure

For each replicate, 75 to 100 adult house flies were removed from the rearing cage by means of a vacuum aspirator, and transferred by carbon dioxide anesthesia to the inner cage containing the mouse. The assembled cage was placed in one of the upper ventilation ports of the chamber. For each experimental situation the test insects were transferred to a clean cage containing the mouse. A house fly candle was placed centrally on the chamber floor and burned for 20 minutes before initiating the repellency counts. The maximum period for the repellency counts was 60 minutes. The first repellency count was made at 10 minutes after the burning ended, and subsequent counts were taken at 5-minute intervals thereafter. The number of house flies repelled were those escaping to the outside cage. For the control, counts were made in a similar manner, but no candle was burned.

The same three candles were used for all four replicates. Between replicates the chamber was exhaused, the Kraft paper flooring for the chamber was replaced, and the two screened repellency cages were submerged in hot detergent water, rinsed and dried.

Results

The average percent of house flies repelled for each 5-minute exposure period through 60 minutes is reported in Table II of U.S. Pat. No. 4,693,890, which is hereby incorporated by reference.

What is claimed is:

1. A process for testing insect repellency and attractancy of molecules using apparatus for such purpose comprising:
   (i) providing active and passive insect interest electronic measuring and recording means;
   (ii) providing enclosable insect feeding or stimulating means having controlled limited access to the external environment surrounding said apparatus and capable of being associated with said measuring and recording means, said insect feeding or stimulating means being located at a fixed insect feeding or stimulating means location defined according to x, y and z coordinates in a first defined 3-space; said insect feeding or stimulating means consisting essentially of:
      (a) an insect feeding or stimulating surface comprising at two spaced electrically conductive elements connected to said measuring and recording means, said elements having such diameters and spacing from one another as to cause an an attracted insect to complete a circuit of electron flow through said conductive elements;
      (b) immediately beneath said insect feeding or stimulating surface a composition of matter comprising molecules to be tested for attractancy and repellency;
      (c) immediately beneath said molecules to be tested, a stimulant or feeding stimulant composition for said insects;
   (iii) providing steady state direct lighting means for supplying a beam of direct light having given substantially constant intensity and wavelength or wavelengths to said feeding or stimulating means location;
   (iv) providing steady state air supply, air conduction and air removal means for supplying, conducting and removing air at a substantially constant mass flow rate and substantially constant linear velocity to, past and from a second 3-space immediately above said insect feeding or stimulating surface simultaneously with the supplying of said beam of direct light to said feeding or stimulating means location substantially immediately above said insect feeding or stimulating surface, said insect feeding or stimulating surface structure being constructed so that said measuring and recording means is sensitive to the completion of a circuit of electron flow through or proximate said conductive elements of said insect feeding or stimulating surface whereby the number and frequency of the insects attracted relative to the attractancy of said direct lighting means to the proximity of said feeding or stimulating means is capable of being determined using said measuring and recording means;
   (v) anaesthetizing selected insects at a location apart from said feeding or stimulating means;
   (vi) then supplying one or more anaesthetized insects to said first defined 3-space;
   (vii) then enclosing said first 3-space surrounding said feeding or stimulating means whereby access thereto is limited to said air supply, air conduction and air removal means;
   (viii) forming an electrical circuit connection between said measuring and recording means and said feeding or stimulating means;
   (ix) then supplying, conducting and removing air at a substantially constant mass flow rate and substantially constant linear velocity to, past and from second defined 3-space;
   (x) simultaneously supplying said direct light to said second defined 3-space, the supplying of light in the air being carried out at such conditions and for such period of time that the anaesthetized insects are de-anaesthetized and recommence life activity; and
   (xi) observing on said measuring and recording means the number and frequency of de-anaesthetized insects attracted to the surface or proximity of said feeding or stimulating means.

2. The process of claim 1 wherein the step of observing and measuring is supplemented with the step of carrying out electrophysiological studies of the neural correlates of attraction and repulsion in the insects.

3. A process for testing insect repellency and attractancy of molecules using apparatus for such purpose comprising:
   (i) providing active and passive interest electronic measuring and recording means;
   (ii) providing enclosable insect feeding or stimulating means having controlled limited access to the external environment surrounding said apparatus and capable of being associated with said measuring and recording means, said insect feeding or stimulating means being located at a fixed insect feeding or stimulating means location defined according to x, y and z coordinates in a first defined 3-space; said insect feeding or stimulating means consisting essentially of:
      (a) an insect feeding or stimulating surface comprising at least two spaced electrically conductive elements connected to said measuring and recording means, said elements having such dimensions and spacing from one another as to cause an attracted insect to complete a circuit of electron flow through or proximite said conductive elements;
(b) immediately beneath said insect feeding or stimulating surface a composition of matter comprising molecules to be tested for attractancy and repellency;
(c) immediately beneath said molecules to be tested, a stimulant or feeding stimulant composition for said insects;

(iii) providing steady state air supply, air conduction and air removal means for supplying, conducting and removing air at a substantially constant mass flow rate and substantially constant linear velocity to, past and from a second 3-space immediately above said insect feeding or stimulating surface, said insect feeding or stimulating surface structure being constructed so that said measuring and recording means is sensitive to the completion of a circuit of electron flow through or proximate said conductive elements of said insect feeding or stimulating surface, whereby the number and frequency of the insects attracted to the proximity of said feeding or stimulating means is capable of being determined using said measuring and recording means;

(iv) anaesthetizing selected insects at a location apart from said feeding or stimulating means;

(v) then supplying one or more anaesthetized insects to said first defined 3-space, said second defined 3-space and a third defined 3-space proximate said first and second defined spaces;

(vi) then enclosing said first defined 3-space surrounding said feeding or stimulating means, said second defined 3-space surrounding said feeding or stimulating means, and said third defined 3-space whereby access thereto is limited to said air supply, said air conduction and said air removal means;

(vii) forming an electrical circuit connection between said measuring and recording means and said feeding or stimulating means;

(viii) then supplying, conducting and removing air at a substantially constant mass flow rate and substantially constant linear velocity to, past and from said second defined 3-space; the supplying of air being carried out at such conditions and for such period of time that the anaesthetized insects are de-anaesthetized and recommence life activities; and (ix) observing on said measuring and recording means the number and frequency of the de-anaesthetized insects attracted to the surface or proximity of said feeding or stimulating means.

4. The process of claim 3 wherein the step of observing and mesuring is supplemented with the step of carrying out electrophysiological studies of the neural correlates of attraction and repulsion in the insects.

5. A process for testing insect repellency and attractancy of molecules using apparatus for such purpose comprising:
(i) providing active and passive insect interest measuring and visual recording means;
(ii) providing enclosable insect stimulating means having controlled limited access to the external environment surrounding said apparatus and capable of being associated with said measuring and recording means, said insect stimulating means being located at a fixed insect stimulating means location defined according to x, y and z coordinates in a first defined 3-space; said insect stimulating means consisting essentially of:
(a) an insect stimulating surface;
(b) immediately beneath said insect stimulating surface a composition of matter comprising molecules to be tested for attractancy and repellency;
(c) immediately beneath said molecules to be tested, a stimulant composition for said insects;

(iii) providing steady state direct lighting means for supplying a beam of direct light having given substantially constant intensity and wavelength or wavelengths to said stimulating means location;

(iv) providing steady state air supply, air conduction and air removal means for supplying, conducting and removing air at a substantially constant mass flow rate and substantially constant linear velocity to, past and from a second 3-space immediately above said insect stimulating surface simultaneously with the supplying of said beam of direct light to said stimulating means location substantially immediately above said insect stimulating surface, said insect stimulating surface structure being constructed so that the number and frequency of the insects attracted relative to the attractancy of said direct lighting means to the proximity of said stimulating means is capable of being determined visually;

(v) anaesthetizing from selected insects at a location apart from said stimulating means;

(vi) then supplying one or more anaesthetized insects to said first defined 3-space;

(vii) then enclosing said first 3-space surrounding said stimulating means whereby access thereto is limited to said air supply, air conduction and air removal means;

(viii) then supplying, conducting and removing air at a substantially constant mass flow rate and substantially constant linear velocity to, past and from said second defined 3-space;

(ix) simultaneously supplying said direct light to said second defined 3-space, the supplying of light and air being carried out at such conditions and for such period of time that the anaesthetized insects are de-anaesthetized and recommence life activity; and (x) observing on said measuring and visual recording means the number and frequency of de-anaesthetized insects attracted to the surface or proximity of said stimulating means.

6. The process of claim 5 wherein the step of observing and mesuring is supplemented with the step of carrying out electro physiological studies of the neural correlates of attraction and repulsion in the insects.

7. A process for testing insect repellency and attractancy of molecules using apparatus for such purpose comprising:
(i) providing active and passive insect interest measuring and visual recording means;
(ii) providing enclosable insect stimulating means having controlled limited access to the external environment surrounding said apparatus and capable of being associated with said measuring and recording means, said insect stimulating means being located at a fixed insect stimulating means location defined according to x, y and z coordinates in a first defined 3-space; said insect stimulating means consisting essentially of:

(a) an insect stimulating surface;
(b) immediately beneath said insect stimulating surface a composition of matter comprising molecules to be tested for attractancy and repellency;
(c) immediately beneath said molecules to be tested, a stimulant composition for said insects;
(iii) providing steady state air supply, air conduction and air removal means for supplying, conducting and removing air at a substantially constant mass flow rate and substantially constant linear velocity to, past and from a second 3-space immediately above said insect stimulating surface, said insect stimulating surface structure being constructed so that the number and frequency of the insects attracted to the proximity of said stimulating means is capable of being determined visually;
(iv) anaesthetizing selected insects at a location apart from said stimulating means;
(v) then supplying one or more anaesthetized insects to said first defined 3-space, said second defined 3-space and a third defined 3-space proximate said first and second defined spaces;
(vi) then enclosing said first defined 3-space surrounding said stimulating means, said second defined 3-space surrounding said stimulating means, and said third defined 3-space whereby access thereto is limited to said air supply, said air conduction and said air removal means;
(vii) then supplying, conducting and removing air at a substantially constant mass flow rate and substantially constant linear velocity to, past and from said second defined 3-space; the supplying of air being carried out at such conditions and for such period of time that the anaesthetized insects are de-anaesthetized and recommence life activities; and
(viii) observing on said measuring and visual recording means the number and frequency of the de-anaesthetized insects attracted to the surface or proximity of said stimulating means.

8. The process of claim 7 wherein the step of observing and mesuring is supplemented with the step of carrying out electro physiological studies of the neural correlates of attraction and repulsion in the insects.

* * * * *